Figure 6:
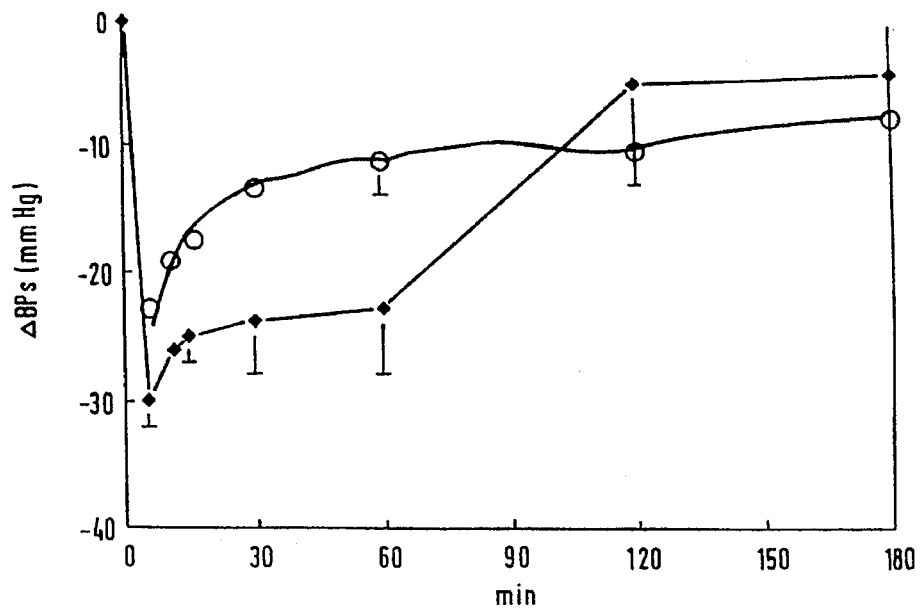
Figure 7:
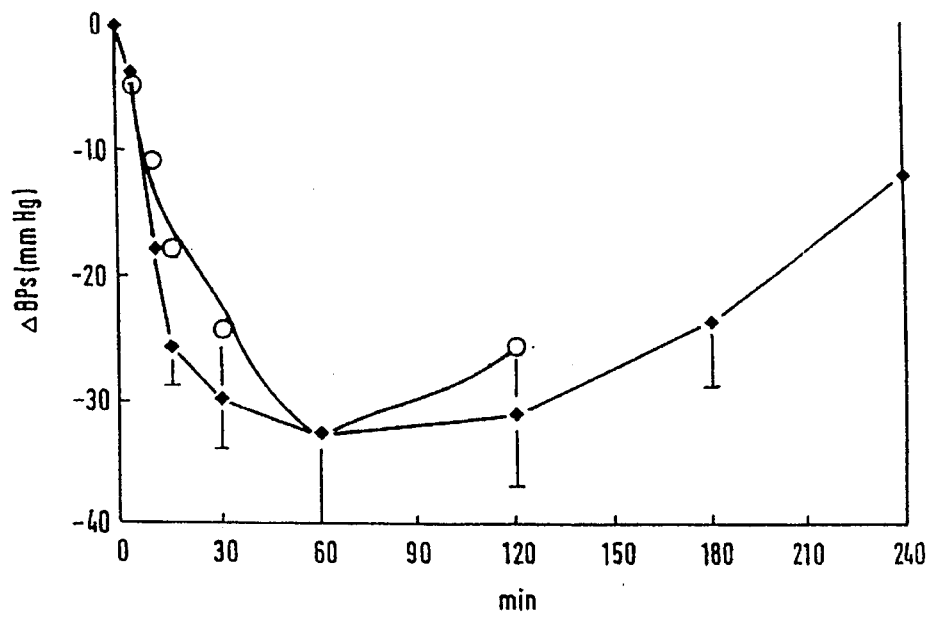

United States Patent [19]

Nallet et al.

[11] Patent Number: 5,591,758

[45] Date of Patent: Jan. 7, 1997

[54] ORGANIC NITRATES, PROCESSES FOR THEIR PREPARATION AND THEIR USE IN THE TREATMENT OF CARDIOVASCULAR DISEASES

[75] Inventors: Jean-Pierre Nallet, Montaney; Jacques Dreux, Lyons; Alain Berdeaux; Vincent Richard, both of Paris, all of France; Piero Martorana, Bad Homburg; Helmut Bohn, Schoneck, both of Germany

[73] Assignee: Laboratoires Hoechst, SA, Puteaux, France

[21] Appl. No.: 971,812

[22] PCT Filed: Aug. 1, 1992

[86] PCT No.: PCT/EP92/01746

§ 371 Date: May 4, 1993

§ 102(e) Date: May 4, 1993

[87] PCT Pub. No.: WO93/03037

PCT Pub. Date: Feb. 18, 1993

[30] Foreign Application Priority Data

Aug. 7, 1991 [FR] France ................................. 91 10039

[51] Int. Cl.$^6$ ..................... C07D 277/06; A01K 31/425
[52] U.S. Cl. ................. 514/365; 514/19; 514/43; 536/24.11; 548/200
[58] Field of Search ............ 548/200; 514/365, 514/14, 43; 536/29.11

[56] References Cited

U.S. PATENT DOCUMENTS 5,385,922  1/1995  Bron ......................... 514/365

Primary Examiner—Robert Gerstl
Attorney, Agent, or Firm—Perman & Green

[57] ABSTRACT

Organic nitrates, processes for their preparation and their use in the treatment of vascular diseases and in particular in the treatment of angina.

The said nitrates correspond to the following formula I:

$$R-CO-(A)_n-Y-B \qquad (I)$$

in which:
R represents, in particular, a sulphur-containing radical and a sulphur-containing amino acid residue; A represents, in particular, a $CH_2$ group or a substituted amino acid; n is 0 or 1 or greater than 1; Y represents an oxygen atom or an NH group and B represents, in particular, a 1,4:3,6-dianhydro hexitol mononitrate radical, an itol nitrate radical or an inositol radical.

The said organic nitrates are prepared by reacting:

I. either a thio acid of the type R—COOH, in which R has the same meaning as above, with a derivative of formula II: $(A)_n-Y-B$, in which A, Y, B and n have the same meaning as above, II. or a derivative of formula III: $R-CO-(A)_n$, in which R, A and n have the same meaning as above, with a derivative of formula Y—B, in which Y and B have the same meaning as above, in an appropriate solvent and under non-epimerising conditions.

7 Claims, 2 Drawing Sheets

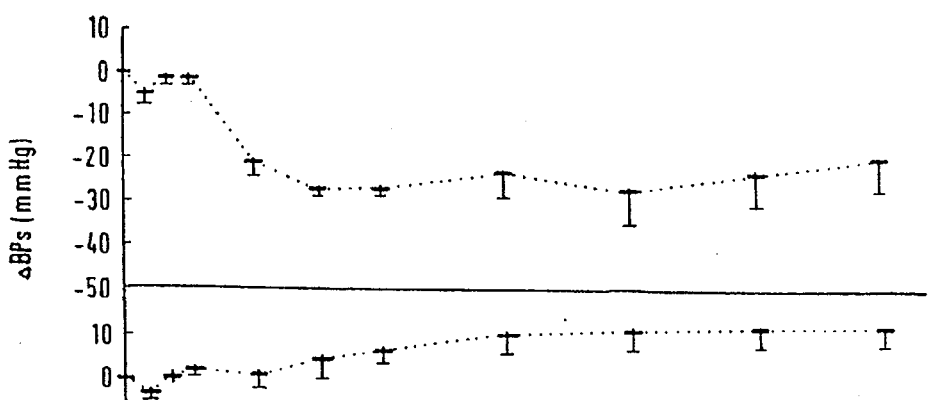
FIG. 1
FIG. 2
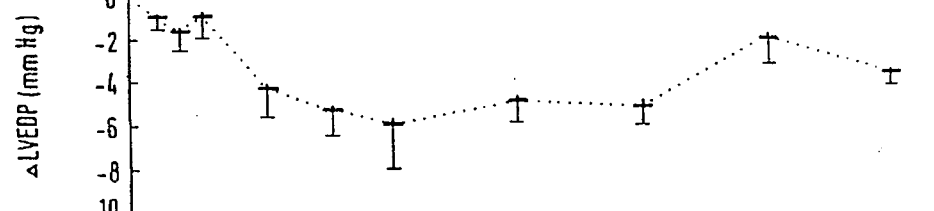
FIG. 3
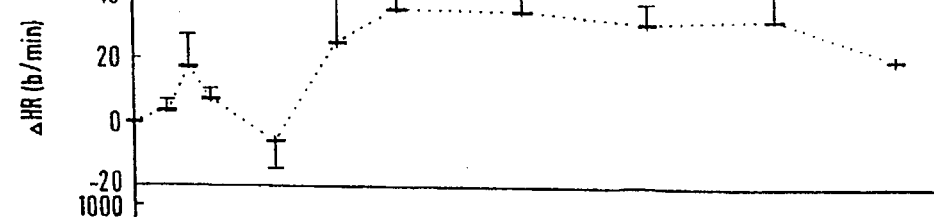
FIG. 4
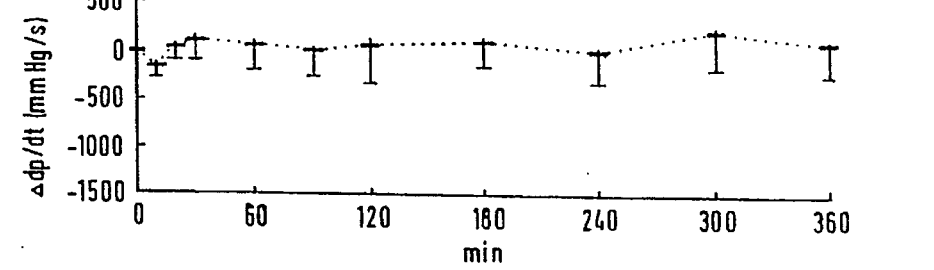
FIG. 5

ORGANIC NITRATES, PROCESSES FOR THEIR PREPARATION AND THEIR USE IN THE TREATMENT OF CARDIOVASCULAR DISEASES

The present invention relates to new organic nitrates, to processes for their preparation and to their use in the treatment of vascular diseases and in particular in the treatment of angina.

An angina pectoris attack results from a sudden and reversible myocardial ischaemia and occurs when the oxygen demands of the myocardium are greater than the supplies from the coronary circulation.

Organic nitrates, which have been used for many years in the treatment of an anginal attack, induce a relaxation of the vascular smooth muscle fibre by raising the level of soluble cyclase guanylate, via nitric oxide formed during the conversion of the nitrates in the presence of cysteine.

In general, their haemodynamic effects are as follows:

venous vasodilation, especially with reduction of the venous return, ventricular filling pressures and the volume of the left ventricle (LV), and therefore reduction in the ventricular parietal tension;

arterial vasodilation: reduction in the post-charge and reduction in the ejection time from the left ventricle; and reflex increase in the heart rate and in the contractility (P. UNGER et al., Rev. Med. Brux., 1989, 10, 82–88).

The leader amongst these products is trinitrin, which has a very rapid action; other derivatives have been developed and have a less rapid and more prolonged action than the latter.

In addition to trinitrin (nitroglycerine), the following may be mentioned as examples of organic nitrates: tetranitroerythritol, hexanitroinositol, tetranitropentaerythritol, propatyl nitrate, isosorbide 5-mononitrate (IS-5-MN), isosorbide dinitrate, isosorbide 2-mononitrate (IS-2-MN), isomannide 2-nitrate and trinitrotriethanolamine, and their substituted derivatives, in particular the aminopropanol derivatives of 1,4:3,6-dianhydrohexitol nitrates.

After penetration into the smooth muscle fibre, the organic nitrates would act by activating cyclase guanylate, in accordance with the following scheme:

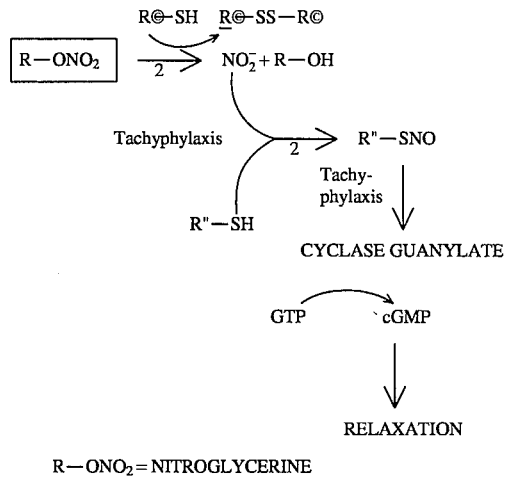

$R-ONO_2$ = NITROGLYCERINE which shows that it is the S-nitrosothiol (R"-SNO), which would activate the cyclase guanylate.

The intracellular depletion of thiol groups would be responsible for the phenomenon of tachyphylaxis to organic nitrates, defined as the loss in activity of a substance during its repeated administration, with the need to increase the dose in order to obtain the same effect.

The prevention of this tachyphylaxis may take several forms:

it may consist in establishing free periods (discontinuous administrations, short-acting formulations) (U. ELKAYAM, Ann. Inter. Med., 1991, 114, 8, 667–677)

simultaneous administration of cysteine derivatives;

the administration of derivatives enabling this tachyphylaxis to be avoided; European Patent Application EP 362 575 describes, for example, fatty acid nitrates bonded to sulphur-containing amino acids, which prevent or attenuate the tachyphylaxis. However, with regard to the compounds described in said application, the recession available is not sufficient either in respect of pharmacology or in respect of toxicology.

The Applicant consequently aimed to provide novel organic nitrates which have a distinctly improved activity (in particular at the level of transport and crossing of cell barriers) and do not give rise to any tachyphylaxis and for which the toxicology and pharmacology of the starting materials is well known.

The present invention relates to organic nitrates, characterised in that they correspond to the following formula I:

$$R-CO-(A)_n-Y-B \qquad (I)$$

in which:

R represents a. one of the following radicals C, D, E, F and G:

(radical C)

in which radical C:

$R_1$ represents a hydrogen atom, a (straight-chain, branched or cyclic) $C_1$ to $C_6$ alkyl group, an optionally substituted phenyl or an optionally substituted benzyl;

$R_2$ represents a hydrogen atom, a (straight-chain, branched or cyclic) $C_1$ to $C_6$ alkyl group, an optionally substituted phenyl, an optionally substituted benzyl, a $C_1$–$C_6$ acyl group, an optionally substituted benzoyl, an alkoxycarbonyl or a CO—X group in which X represents a radical C or a radical D, E, F or G as defined below, and m represents 1 (5-centred ring) or 2 (5-centred ring);

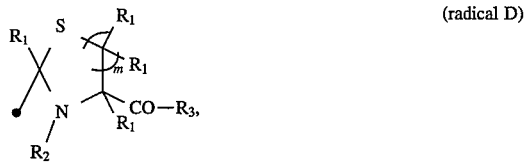

(radical D)

in which radical D:

$R_1$ and $R_2$ have the same meaning as above;

$R_3$ represents an OH group, a (straight-chain, branched or cyclic) $C_1$ to $C_6$ O-alkyl group, an optionally substituted O-phenyl group, an optionally substituted O-benzyl group, a radical E as defined above, a radical of the type Y—B— or an NH—CH(COOR$_3$)CH$_2$—S—R$_4$ group, in which $R_4$ represents a hydrogen atom, a (straight-chain, branched or cyclic) $C_1$ to $C_6$ alkyl group, an optionally substituted phenyl, an optionally substituted S-phenyl, an optionally substituted benzyl or one of the following groups: CH₃—CO—NH—CH₂, B—Y—CO—CH(NH—COO—C(CH₃)₃)CH₂—S, or B—Y—CO—CH(NH₂.HCl)CH₂—S, B and Y being as defined above, and m represents 1 or 2;

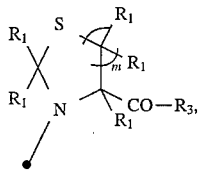
(radical E)

in which radical E:
R₁, R₃ and m have the same meaning as above;

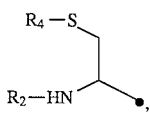
(radical F)

in which radical F:
R₂ and R₄ have the same meaning as above;

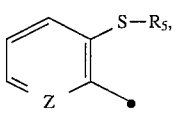
(radical G)

in which radical G:
R₅ represents a hydrogen atom, a (straight-chain, branched or cyclic) C₁ to C₆ alkyl group, an optionally substituted phenyl, an optionally substituted S-phenyl, an optionally substituted benzyl or a CH₃—CO—NH—CH₂ or B—Y—CO—C₅ZH₃—S group and Z represents CH or N;

b. an optionally protected sulphur-containing amino acid residue; or c. R also represents, when n is other than 0 and A is a sulphur-containing radical H or I as defined below, an OH group, a (straight-chain, branched or cyclic) C₁-C₆ O-alkyl group, an optionally substituted O-phenyl group, an optionally substituted O-benzyl group, a radical E as defined above or a radical Y—B, B and Y being as defined below;

A represents a CH₂ group, a substituted or unsubstituted amino acid, with the acid group bonded to Y and the amino group bonded to CO, or one of the following radicals:

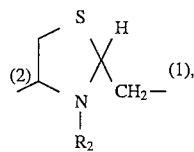
(radical H)

in which radical H:
R₂ represents a hydrogen atom, a (straight-chain, branched or cyclic) C₁ to C₆ alkyl group, an optionally substituted phenyl, an optionally substituted benzyl, a C₁ to C₆ acyl group, an optionally substituted benzoyl, an alkoxycarbonyl group or a group CO—X in which X represents one of the radicals C, D, E, F or G as defined above for R, (1) is the bond with Y, and (2) is the bond with R—CO; or

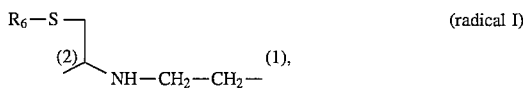
(radical I)

in which radical I:
R₆ represents a hydrogen atom, a (straight-chain, branched or cyclic) C₁ to C₆ alkyl group, an optionally substituted phenyl, a substituted S-phenyl, an optionally substituted benzyl or one of the following groups: CH₃—CO—NH—CH₂, S—CH₂—CH—(CO—R₇)—NH—CH₂—CH₂—NH—B in which R₇ represents an OH group, a C₁-C₆ O-alkyl group, an optionally substituted O-phenyl group, an optionally substituted O-benzyl group, a radical E as defined above or a radical Y—B, B and Y being as defined below, and (1) and (2) have the same meaning as above;

n is 0 or 1 or greater than 1;

Y represents an oxygen atom or an NH group;

B represents:

α) a 1,4:3,6-dianhydro hexitol mononitrate radical of formula (a)

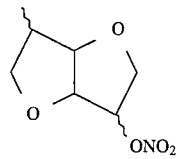

β) a C₁ to C₆ itol nitrate radical of formulae (b)

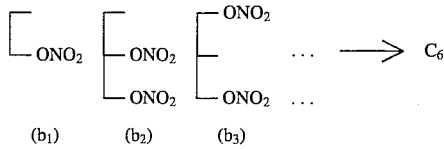

γ) an inositol "p"-nitrate radical, p being an integer from 1 to 5, of formula (c)

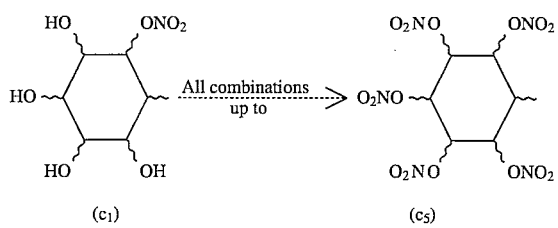

δ) one of the following groups:
  a —CH₂—C(CH₂—ONO₂)₃ group, derived from pentaerythritol,
  a —CH₂—C(C₂H₅)(CH₂—ONO₂)₂ group, derived from ethyltrimethylolmethane, or
  a —CH₂—CH₂—N(CH₂—CH₂—ONO₂)₂ group, derived from triethanolamine,
with all OH and ONO₂ combinations.

The compounds of formula I according to the invention encompass their various isomers.

In the present invention, the substituents of the substituted phenyl and substituted benzyl groups are advantageously chosen from the following groups: NO₂, halogen and CV₃ in which V represents a halogen or a lower alkyl.

Organic nitrates are thus obtained which, surprisingly, both have a distinctly improved activity compared with the nitrates of the prior art and do not give rise to tachyphylaxis. Such nitrates are particularly useful as vaso-relaxants, in particular in the treatment of some cardiovascular diseases and more particularly in the treatment of angina pectoris.

They also have the advantage of having pharmacological and toxicological data similar to those of the known organic nitrates which may, moreover, serve as controls.

According to an advantageous embodiment of the invention, the preferred compounds of formula I contain the following radicals for R, A, Y and B respectively:

R represents one of the following radicals:

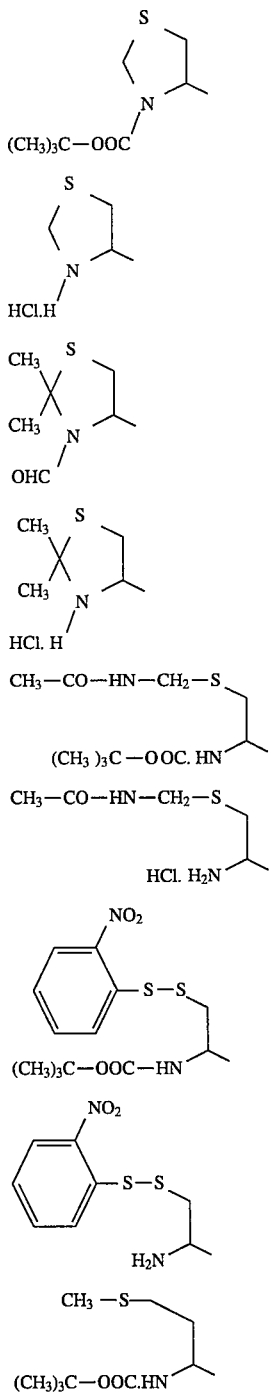

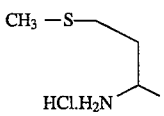
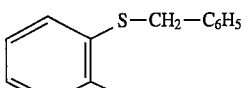
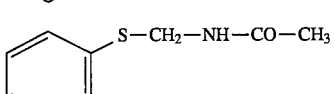
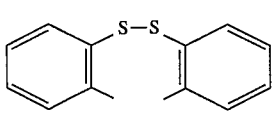

A represents an optionally substituted amino acid radical, when n is other than 0, and in particular glycine and its derivatives, proline and its derivatives, alanine and its derivatives, valine and its derivatives and phenylalanine and its derivatives;

Y represents an oxygen atom or an NH group; and

B is a radical derived from the following compounds:

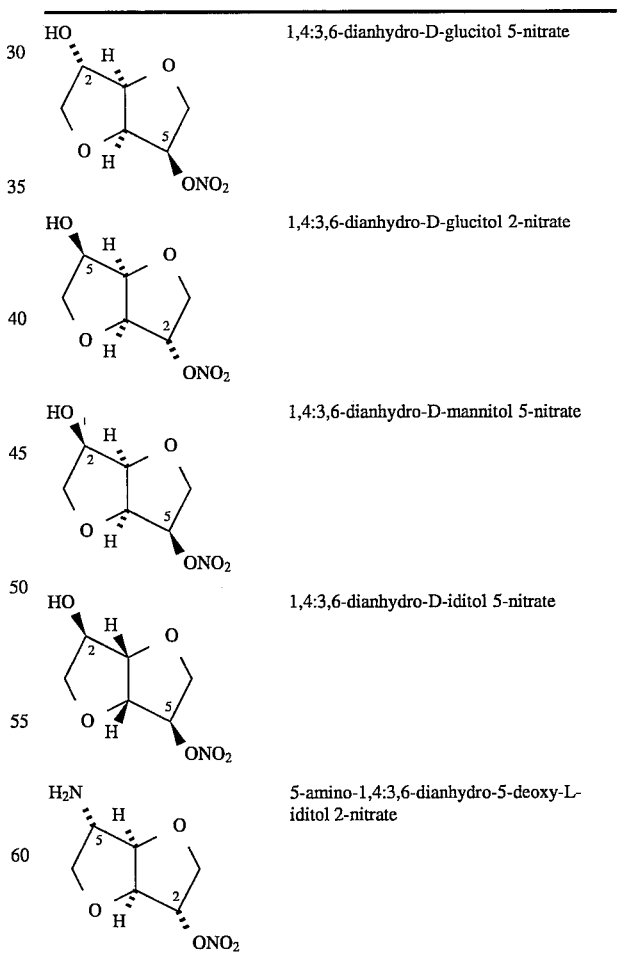

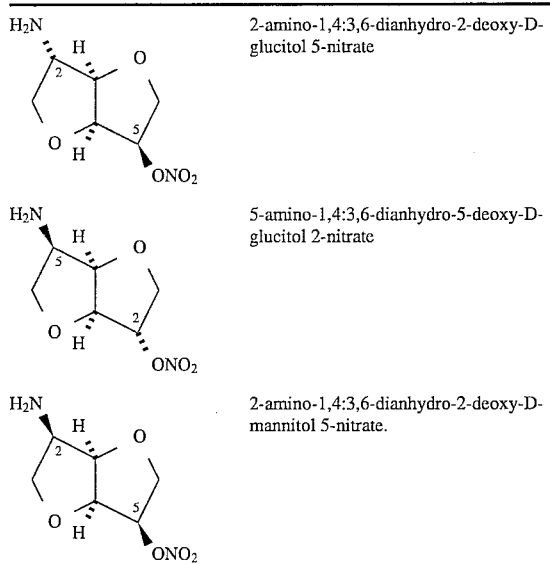

| | |
|---|---|
| | 2-amino-1,4:3,6-dianhydro-2-deoxy-D-glucitol 5-nitrate |
| | 5-amino-1,4:3,6-dianhydro-5-deoxy-D-glucitol 2-nitrate |
| | 2-amino-1,4:3,6-dianhydro-2-deoxy-D-mannitol 5-nitrate. |

In general, the organic nitrates according to the invention contain a thio acid R—COOH associated with an organic nitrate of the itol or dianhydro itol type at an OH or NH group of the said nitrate. Several radicals are thus distinguished according to the radical R of the acid associated with the nitrate:

thioproline and its derivatives (radicals C, D, E);

cysteine derivatives (radical F) and derivatives of other sulphur-containing amino acids; and derivatives of thiosalicylic acid (radical G) or of 3-mercaptopicolinic acid.

Surprisingly, all of these products show both an activity on the cardiovascular system (vasorelaxant activity), and in particular an antianginal activity, and a reduction in the tachyphylaxis phenomenon.

The present invention also relates to a process for the preparation of an organic nitrate according to the invention, characterised in that:

I. either a thio acid of the type R—COOH, in which R has the same meaning as above, is reacted with a derivative of formula II: $(A)_n$—Y—B, in which A, Y, B and n have the same meaning as above, II. or a derivative of formula III: R—CO—$(A)_n$, in which R, A and n have the same meaning as above, is reacted with a derivative of formula Y—B, in which Y and B have the same meaning as above, in an appropriate solvent and under non-epimerising conditions.

Advantageously, the solvent is in particular, and in a non-limiting manner: dichloromethane, acetonitrile, dimethylformamide, ethyl acetate or tetrahydrofuran.

According to an advantageous embodiment of the said process, the derivatives of formula II are chosen from:

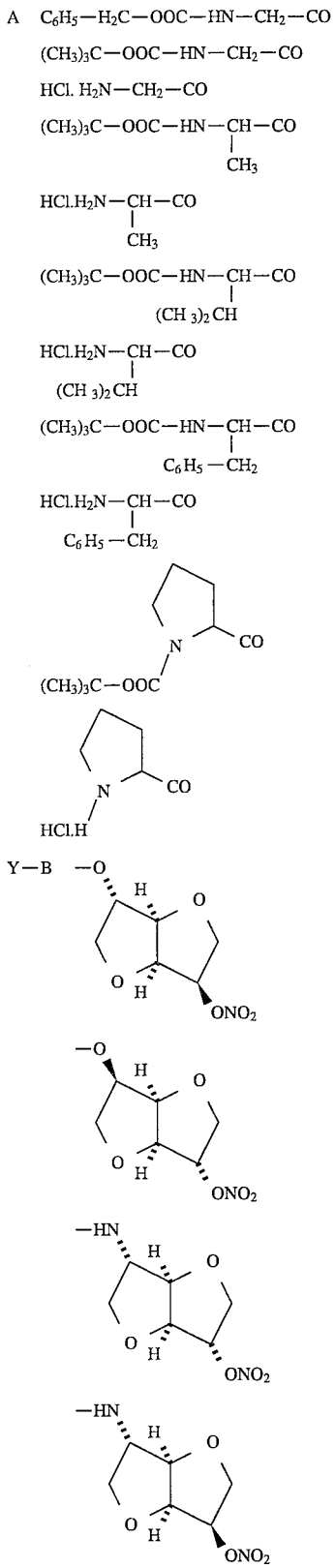

According to another advantageous embodiment of the said process, the derivative of formula III is:

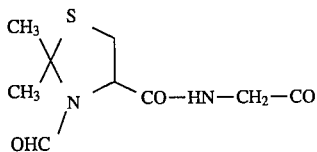

Surprisingly, the derivatives of formula II have an activity on the cardiovascular system and in particular an antianginal activity.

Both the derivatives of formula I and the derivatives of formula II find application as medicaments in the treatment of cardiovascular diseases and in particular in the treatment of angina pectoris.

In addition to the above provisions, the invention also comprises other provisions, which will become apparent from the description which follows and which relates to examples of implementation of the process which is the subject of the present invention.

However, it must be clearly understood that these examples are given solely by way of illustration of the subject of the invention and in no way constitute a limitation thereof.

EXAMPLES

I—SYNTHESIS OF THE INTERMEDIATES

I-a: of the type $(A)_n$—Y—B of formula II, where n=1:

Table I below shows the various derivatives synthesised.

TABLE I

| Amino acids | Y–B Organic nitrates | | | |
|---|---|---|---|---|
| | —O⟨isosorbide-ONO₂⟩ | —O⟨isosorbide-ONO₂⟩ (isomer) | —HN⟨isosorbide-ONO₂⟩ | —HN⟨isosorbide-ONO₂⟩ (isomer) |
| A  $C_6H_5$—$H_2C$—OOC—HN—$CH_2$—CO | 1 | 2 | 3 | 4 |
| $(CH_3)_3C$—OOC—HN—$CH_2$—CO | | | | 5 |
| HCl.$H_2N$—$CH_2$—CO | | | | 6 |
| $(CH_3)_3C$—OOC—HN—CH—CO<br>　　　　　　　　　\|<br>　　　　　　　　　$CH_3$ | | | | 7 |
| HCl.$H_2N$—CH—CO<br>　　　　　\|<br>　　　　　$CH_3$ | | | | 8 |
| $(CH_3)_3C$—OOC—HN—CH—CO<br>　　　　　　　　　\|<br>　　　　　　　　　$(CH_3)_2CH$ | | | | 9 |
| HCl.$H_2N$—CH—CO<br>　　　　　\|<br>　　　　　$(CH_3)_2CH$ | | | | 10 |
| | | | | 15 |
| | | | | 16 |

TABLE I-continued

| Amino acids | Y—B Organic nitrates | | | |
|---|---|---|---|---|
| | structure 1 | structure 2 | structure 3 | structure 4 |
| (CH₃)₃C—OOC—HN—CH—CO<br>　　　　　　　　　｜<br>　　　　　　　　CH₂<br>　　　　　　　　　｜<br>　　　　　　　　C₆H₅ | | | 11 | |
| HClH₂N—CH—CO<br>　　　　　｜<br>　　　　CH₂<br>　　　　　｜<br>　　　　C₆H₅ | | | | 12 |
| structure (proline N-Boc) | | | 13 | |
| structure (proline·HCl) | | | | 14 |

In the examples which follow, the abbreviations used have the following meanings:

Boc for butoxycarbonyl
DCC for 1,3-dicyclohexylcarbodiimide
DCU for 1,3-dicyclohexylurea
HOBt for 1-hydroxybenzotriazole hydrate
CMC for 1-cyclohexyl-3-(2-morpholinoethyl)carbodiimide metho-p-toluenesulphonate
CMU for 1-cyclohexyl-3-(2-morpholinoethyl)urea metho-p-toluenesulphonate
CBZ for benzyloxycarbonyl.

EXAMPLE 1

N-[(t-Butoxy)carbonyl]glycine ester of 5-O-nitro-1,4:3,6-dianhydro-D-glucitol (1)

1 g of (5.23 mmol) of 1,4:3,6-dianhydro-D-glucitol 5-nitrate, 0.92 g (5.25 mmol) of N-t-Boc-glycine, 2.22 g (5.24 mmol) of CMC and 0.08 g (0.52 mmol) of 4-pyrrolidinopyridine are stirred for 24 hours at ambient temperature in 40 ml of dichloromethane (stabilised on amylene and dried over alumina). After filtering off CMU, 50 ml of dichloromethane are added and the solution is washed successively with 30 ml of a 5% solution of acetic acid, 30 ml of water, 30 ml of a half-saturated sodium bicarbonate solution and three times with 30 ml of water and then dried over sodium sulphate. After filtration and evaporation of the filtrate, the product is recrystallised from ethyl acetate. 0.85 g is obtained (Yield= 47%). m.p.=130°–131° C.

Analysis

|  | C | H | N |
|---|---|---|---|
| Calc. (0.45 H$_2$O) | 43.80 | 5.90 | 7.85 |
| Found | 43.9 | 5.7 | 7.7 |

EXAMPLE 2

Glycine ester of 5-O-nitro-1,4:3,6-dianhydro-D-glucitol monohydrochloride (2)

6.6 g of the above product (1) are added to 45 ml of a 2N hydrochloric acid solution in ethyl acetate. The solution is stirred for 10 hours at ambient temperature and the precipitate formed is filtered off and washed with ether and then recrystallised from methanol. 3.2 g of purified product are obtained (Yield=59%).

m.p.=196° C. (dec), $[\alpha]_D^{20}$=+113.5 (c 0.6 water).

Analysis H

|  | C | H | N | O |
|---|---|---|---|---|
| Calc. (0.16 H$_2$O) | 33.40 | 4.66 | 9.73 | 39.81 |
| Found | 33.4 | 4.6 | 9.6 | 40.1 |

EXAMPLE 3

Glycine ester of 2-O-nitro-1,4:3,6-dianhydro-D-glucitol monohydrochloride (3)

4 g (20.9 mmol) of 1,4:3,6-dianhydro-D-glucitol 2-nitrate, 3.4 g (19.4 mmol) of N-t-Boc-glycine, 8.8 g (20.9 mmol) of CMC and 0.28 g (2 mmol) of 4-pyrrolidinopyridine are stirred for 24 hours at ambient temperature in 120 ml of dichloromethane (stabilised on amylene and dried over alumina). After filtering off CMU, 130 ml of dichloromethane are added and the solution is washed and dried as for (1). 5.85 g of an oil corresponding to the expected product are isolated. This oil is dissolved in 42 ml of a 2N hydrochloric acid solution in ethyl acetate. After 10 hours at ambient temperature, the precipitate formed is filtered off and washed with ether and then recrystallised from anhydrous methanol. 2.5 g are obtained (Yield=45%).

m.p.=188°–189° C. (dec), $[\alpha]_D^{20}$=+88.1 (c 0.6 water).

Analysis

|  | C | H | N |
|---|---|---|---|
| Calc. | 33.75 | 4.60 | 9.84 |
| Found | 34.0 | 4.6 | 9.8 |

EXAMPLE 4

N-[(Benzyloxy)carbonyl]glycine amide of 5-amino-5-deoxy-2-O-nitro-1,4:3,6-dianhydro-L-iditol (4)

A solution of 1.43 g (7.5 mmol) of 5-amino-1,4:3,6-dianhydro-5-deoxy-L-iditol 2-nitrate in 70 ml of anhydrous dichloromethane is stirred at ambient temperature. 1.54 g (7.41 mmol) of N-CBZ-glycine and 1.523 g (7.41 mmol) of DCC are added successively. After reaction for 24 hours, filtering off DCU and evaporation of the solvent, the oil obtained is chromatographed (silica, 230–400 mesh ASTM). The compound isolated is crystallised with ether and then recrystallised from a mixture of ethyl acetate/diisopropyl ether. 2 g are obtained (Yield=70%).

m.p.=75°–76° C., $[\alpha]_D^{20}$=+24.7 (c 1, ethanol)

Analysis

|  | C | H | N |
|---|---|---|---|
| Calc. | 50.39 | 5.02 | 11.01 |
| Found | 50.2 | 5.1 | 10.9 |

EXAMPLE 5

N-[(t-Butoxy)carbonyl]glycine amide of 5-amino-5-deoxy-2-O-nitro-1,4:3,6-dianhydro-L-iditol (5)

A solution of 6 g (31.5 mmol) of 5-amino-1,4:3,6-dianhydro-5-deoxy-L-iditol 2-nitrate in 270 ml of anhydrous dichloromethane is stirred at ambient temperature. 5.4 g (30.8 mmol) of N-t-Boc-glycine and 6.4 g (31 mmol) of DCC are added successively. After reaction for 24 hours, filtering off DCU and evaporation of the solvent, the product is chromatographed on silica (230–400 mesh ASTM) and the compound isolated is recrystallised from methanol. 7.75 g are obtained (Yield=72%).

m.p.=118° C.

EXAMPLE 6

Glycine amide of 5-amino-5-deoxy-2-O-nitro-1,4:3,6-dianhydro-L-iditol monohydrochloride (6)

4.75 g of the above compound (5) are added to 35 ml of a 1.7N hydrochloric acid solution in methanol. The solution is stirred for 10 hours at ambient temperature and the precipitate formed is filtered off and washed with anhydrous ether. The product is recrystallised from methanol; 3.3 g are obtained (Yield=85%).

m.p.=198° C. (dec), $[\alpha]_D^{20}$=−2.5 (c 1, water)

Analysis

|  | C | H | N | Cl |
|---|---|---|---|---|
| Calc. | 33.87 | 4.97 | 14.81 | 12.49 |
| Found | 34.1 | 4.8 | 14.7 | 12.3 |

The base form of this compound is prepared as follows: ammonia is bubbled into a suspension of 2.35 g of (6) at ambient temperature and with stirring. The ammonium chloride formed is filtered off and after evaporation of the solvent a crystallisation of the residual oil is observed. After recrystallisation from an ethyl acetate/diisopropyl ether mixture, 1.85 g are obtained (Yield=90%).

m.p.=81° C.

EXAMPLE 7

N-[(t-Butoxy)carbonyl]-L-alanine amide of
5-amino-5-deoxy-2-O-nitro-1,4:3,6-dianhydro-L-iditol
(7)

A solution of 2 g (10.5 mmol) of 5-amino-1,4:3,6-dianhydro-5-deoxy-L-iditol 2-nitrate in 70 ml of anhydrous dichloromethane is stirred at ambient temperature. 2 g (10.5 mmol) of N-t-Boc-L-alanine, 4.46 g (10.5 mmol) of CMC and 1.42 g (10.5 mmol) of HOBt are added successively. After reaction for 24 hours, dichloromethane is added and the organic phase is washed and dried as for (1). 3.15 g of a solid are isolated, which solid is recrystallised from methanol. 2.15 g are obtained (Yield=56%).

m.p.=133° C., $[\alpha]_D^{20}$=+15.8 (c 0.6, ethanol)

Analysis

|  | C | H | N |
|---|---|---|---|
| Calc. | 46.53 | 6.41 | 11.62 |
| Found | 46.8 | 6.4 | 11.5 |

EXAMPLE 8

L-Alanine amide of
5-amino-5-deoxy-2-O-nitro-1,4:3,6-dianhydro-L-iditol
monohydrochloride (8)

3.05 g of the above compound (7) are added to 38 ml of a 1.7N hydrochloric acid solution in methanol. The suspension is stirred for 24 hours at ambient temperature (the mixture becomes clear after a reaction time of 3 hours), then concentrated under vacuum and a white solid is precipitated by adding ether. 2.6 g of solid are obtained, which solid is recrystallised from methanol. 2.1 g are finally recovered (Yield=83%).

m.p.=189° C. (dec), $[\alpha]_D^{20}$=+9.3 (c 0.6, water)

Analysis

|  | C | H | N | Cl |
|---|---|---|---|---|
| Calc. | 36.31 | 5.42 | 14.11 | 12.90 |
| Found | 36.5 | 5.5 | 14.2 | 11.9 |

EXAMPLE 9

N-[(t-Butoxy)carbonyl]-L-valine amide of
5-amino-5-deoxy-2-O-nitro-1,4:3,6-dianhydro-L-iditol
(9)

A solution of 3.4 g (17.8 mmol) of 5-amino-1,4:3,6-dianhydro-5-deoxy-L-iditol 2-nitrate in 220 ml of anhydrous dichloromethane is stirred at ambient temperature. 3.7 g (17 mmol) of N-t-Boc-L-valine, 7.56 g (17.8 mmol) of CMC and 2.4 g (17.8 mmol) of HOBt are added successively. After a reaction time of 21 hours, dichloromethane is added and the subsequent procedure is as for the preparation of (1); the solid is then recrystallised from a methanol/petroleum ether mixture; 3.55 g are obtained (Yield=54%).

m.p.=130°–131° C., $[\alpha]_D^{20}$=+30.66 (c 0.6, ethanol)

Analysis

|  | C | H | N |
|---|---|---|---|
| Calc. | 49.35 | 6.98 | 10.79 |
| Found | 49.4 | 6.7 | 10.6 |

The treatment of this compound with a 2N hydrochloric acid solution in ethyl acetate enables the t-butoxycarbonyl group to be removed and leads to the hydrochloride of the corresponding amine (10). This compound has not been recrystallised.

EXAMPLE 10

N-[(t-Butoxy)carbonyl]-L-phenylalanine amide of
5-amino-5-deoxy-2-O-nitro-1,4:3,6-dianhydro-L-iditol
(11)

A solution of 3.8 g (20 mmol) of 5-amino-1,4:3,6-dianhydro-5-deoxy-L-iditol 2-nitrate in 250 ml of anhydrous dichloromethane is stirred at ambient temperature. 5.2 g (19.6 mmol) of N-t-Boc-L-phenylalanine, 8.48 g (20 mmol) of CMC and 2.7 g (20 mmol) of HOBt are added successively. After a reaction time of 24 hours, the subsequent procedure is as for the preparation of (1); the solid is then recrystallised from absolute ethanol; 4.45 g of a white solid are obtained (Yield=52%).

m.p.=157°–159° C., $[\alpha]_D^{20}$=+25 (c 0.6, ethanol)

Analysis

|  | C | H | N |
|---|---|---|---|
| Calc. | 54.91 | 6.22 | 9.60 |
| Found | 54.7 | 6.2 | 9.6 |

EXAMPLE 11

L-phenylalanine amide of
5-amino-5-deoxy-2-O-nitro-1,4:3,6-dianhydro-L-iditol
monohydrochloride (12)

4.2 g of the above compound (11) are added to 50 ml of a 2N hydrochloric acid solution in methanol. The mixture is stirred for 20 hours at ambient temperature and then concentrated under vacuum and the viscous mass obtained is chromatographed on silica (230–400 mesh ASTM). An oil is isolated, which is treated with ethanol; the insoluble oily fraction is removed and a white solid is precipitated from the ethanol phase by adding ether. The product is recrystallised from a methanol/diisopropyl ether mixture. 2.15 g of product are obtained (Yield=60%).

m.p.=175° C. (dec), $[\alpha]_D^{20}$=+53 (c 0.6, water)

Analysis

|  | C | H | N |
|---|---|---|---|
| Calc. (0.7 H$_2$O) | 46.62 | 5.57 | 10.87 |
| Found | 46.5 | 5.4 | 10.9 |

EXAMPLE 12

N-[(t-Butoxy)carbonyl]-L-proline amide of 5-amino-5-deoxy-2-O-nitro-1,4:3,6-dianhydro-L-iditol (13)

A solution of 2.5 g (13.1 mmol) of 5-amino-1,4:3,6-dianhydro-5-deoxy-L-iditol 2-nitrate in 125 ml of anhydrous dichloromethane is stirred at ambient temperature. 2.8 g (13.0 mmol) of N-t-Boc-L-proline, 5.5 g (13 mmol) of CMC and 1.75 g (13 mmol) of HOBt are added successively. After a reaction time of 24 hours, the subsequent procedure is as for the preparation of (1); the solid obtained is recrystallised from ethyl acetate; 2.9 g are obtained (Yield=57%).

m.p.=117°–118° C., $[\alpha]_D^{20}$=+5.2 (c 0.6, ethanol)

Analysis

|  | C | H | N |
|---|---|---|---|
| Calc. | 49.60 | 6.50 | 10.84 |
| Found | 49.7 | 6.7 | 10.6 |

EXAMPLE 13

L-Proline amide of 5-amino-5-deoxy-2-O-nitro-1,4:3,6-dianhydro-L-iditol monohydrochloride (14)

3.3 g of the above compound (13) are added to 17 ml of a 2.2N hydrochloric acid solution in methanol. The mixture is stirred for 20 hours at ambient temperature and then concentrated under vacuum and the product is precipitated by adding ether. After recrystallisation from ethanol, 2.2 g of a white solid are obtained (Yield=80%).

m.p.=173° C., $[\alpha]_D^{20}$=−28.1 (c 0.6, water)

Analysis

|  | C | H | N | Cl |
|---|---|---|---|---|
| Calc. | 40.81 | 5.60 | 12.97 | 10.95 |
| Found | 40.7 | 5.8 | 12.8 | 11.1 |

EXAMPLE 14

N-[(t-Butoxy)carbonyl]glycine amide of 2-amino-2-deoxy-5-O-nitro-1,4:3,6-dianhydro-D-glucitol (15)

A solution of 4 g (21 mmol) of 2-amino-1,4:3,6-dianhydro-2-deoxy-D-glucitol 5-nitrate in 180 ml of anhydrous dichloromethane is stirred at ambient temperature. 3.6 g (20.5 mmol) of N-t-Boc-glycine and 4.28 g (20.7 mmol) of DCC are added successively. After reaction for 24 hours, filtering off DCU and evaporation of the solvent, the product is chromatographed on silica (230–400 mesh ASTM). The compound isolated is recrystallised from an ethyl acetate/diisopropyl ether mixture; 4.8 g are obtained (Yield=67 %).

m.p.=112°–113° C., $[\alpha]_D^{20}$=+101.8 (c 0.6, ethanol)

Analysis

|  | C | H | N |
|---|---|---|---|
| Calc. | 44.95 | 6.09 | 12.10 |
| Found | 45.0 | 6.2 | 12.0 |

EXAMPLE 15

Glycine amide of 2-amino-2-deoxy-5-O-nitro-1,4:3,6-dianhydro-D-glucitol monohydrochloride (16)

7.3 g of the above compound (15) are added to 60 ml of a 1.85N hydrochloric acid solution in ethanol. The mixture is stirred for 16 hours at ambient temperature and the precipitate formed is filtered off and washed with anhydrous ether. This compound is recrystallised from methanol and 2.95 g of white solid are obtained (Yield=49%).

m.p.=193°–194° C., $[\alpha]_D^{20}$=+95 (c 0.6 water).

Analysis

|  | C | H | N | Cl |
|---|---|---|---|---|
| Calc. | 33.87 | 4.87 | 14.81 | 12.49 |
| Found | 33.7 | 5.1 | 14.6 | 12.5 |

I-b: of the type $(A)_n$—Y—B where n=2:

EXAMPLE 16

5-[[2-[[((2S)-2-pyrrolidinyl)carbonyl]amino]-1-oxoethyl]amino]-5-deoxy-2-O-nitro-1,4:3,6-dianhydro-L-iditol monohydrochloride (49)

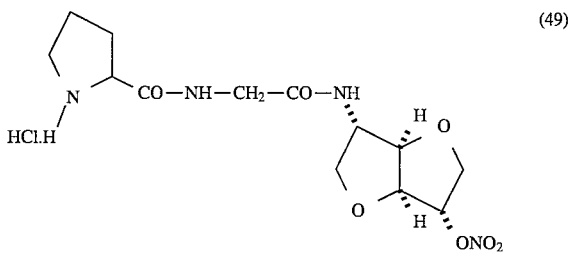

(49)

A solution of 5.35 g (21.6 mmols) of base form corresponding to (6) in 190 ml of anhydrous dichloromethane is stirred at ambient temperature. 4.65 g (21.6 mmols) of N-t-Boc-L-proline, 4.46 g (21.6 mmols) of DCC and 2.92 g (21.6 mmols) of HOBt are added successively. After a reaction time of 24 hours, the DCU is filtered off and the solvent is evaporated. The oil is chromatographed on silica (230–400 mesh ASTM) and 7.8 g (yield=81%) of the expected compound are isolated. It was not possible to crystallise the latter; it is treated directly.

The 7.8 g of the above compound are added to 60 ml of a 2N solution of hydrochloric acid in ethyl acetate. The solution is stirred for 6 hours at ambient temperature and the white solid formed is filtered off and washed with ethyl acetate and then with ether. After recrystallisation from ethanol and then from methanol, 4.5 g of product are obtained (yield=67%).

m.p.=179° C. (dec), $[\alpha]_D^{20}$=−21.1 (c 1, water).

Analysis

|  | C | H | N | Cl |
|---|---|---|---|---|
| Calc. (0.04 HCl) | 40.85 | 5.50 | 14.65 | 9.64 |
| Found | 40.7 | 5.5 | 14.6 | 9.6 |

I-c: of the type R—CO—A of formula III:

EXAMPLE 17

N-[(3-Formyl-2,2-dimethyl-4-L-thiazolidinyl)carbonyl]glycine (17)

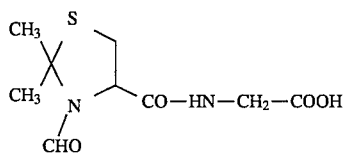

(17)

This compound is prepared by saponification of the corresponding ester.

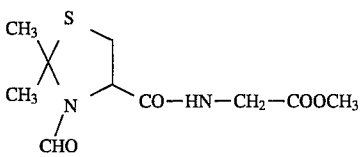

the synthesis of which is described by KING et al., J. Chem. Soc. 1957, 880–885.

A solution of 6.24 g of ester in 63 ml of dioxane is stirred at room temperature and 25.8 ml of a 1N sodium hydroxide solution are added. After a reaction time of one hour, the solution is concentrated and acidified with 25 ml of a 1N hydrochloric acid solution. The white precipitate is filtered off and washed with carbon tetrachloride and then with ether. 4.35 g of acid of a purity sufficient for use in the following step are obtained (Yield=74%).

II — SYNTHESIS OF THE COMPOUNDS OF FORMULA I where n = 0.

Table II below shows the various derivatives synthesised.

| R | Y—B (Organic nitrates) | | | |
|---|---|---|---|---|
| | isosorbide -O-...ONO$_2$ (isomer A) | isosorbide -O-...ONO$_2$ (isomer B) | isosorbide -HN-...ONO$_2$ (isomer A) | isosorbide -HN-...ONO$_2$ (isomer B) |
| (CH$_3$)$_3$C—OOC—N(thiazolidine)— | 18 | 24 | 50 | 40 |
| (CH$_3$)$_3$C—OOC—N(thiazolidine)— · HCl.H | 19 | 25 | 30 | |
| OHC—N[C(CH$_3$)$_2$—S]— | | | 31 | |
| HCl.H · —N[C(CH$_3$)$_2$—S]— | | | 32 | |
| CH$_3$—CO—HN—CH$_2$—S—CH$_2$—CH(CH$_3$)—HN—OOC—C(CH$_3$)$_3$ | 20 | 26 | 33 | 41 |

II — SYNTHESIS OF THE COMPOUNDS OF FORMULA I where n = 0.

Table II below shows the various derivatives synthesised.

| R | Y–B Organic nitrates | | | |
|---|---|---|---|---|
| | (isosorbide-2-O-, 5-ONO₂) | (isomannide-2-O-, 5-ONO₂) | (isomannide-2-HN-, 5-ONO₂) | (isoidide-2-HN-, 5-ONO₂) |
| CH₃—CO—HN—CH₂—S— | 21 | 27 | 34 | 42 |
| HCl.H₂N-CH(CH₃)-CH₂-CH₂-S— | | | | |
| NO₂-C₆H₄-S—S-CH₂-CH(CH₃)-HN-OOC-C(CH₃)₃ | | | 35 | |
| NO₂-C₆H₄-S—S-CH₂-CH(CH₃)-NH₂ | | | 36 | |
| CH₃—S-CH₂-CH(CH₃)-HN-OOC-C(CH₃)₃ | | | 37 | 43 |
| CH₃—S-CH₂-CH(CH₃)-NH₂.HCl | | | 38 | 44 |

II — SYNTHESIS OF THE COMPOUNDS OF FORMULA I where n = 0.

Table II below shows the various derivatives synthesised.

| R | Y—B Organic nitrates | | | |
|---|---|---|---|---|
| S—CH$_2$—C$_6$H$_5$ (o-tolyl) | 22 | 28 | | |
| S—CH$_2$—NH—CO—CH$_3$ (o-tolyl) | 23 | 29 | 39 | 45 |
| S—S—(o-tolyl)(phenyl) | | | | |
| thiazolidine-N—CO—CH$_3$ | | | 51 | |
| thiazolidine-N—CO—C$_6$H$_4$ | | | 52 | |

II — SYNTHESIS OF THE COMPOUNDS OF FORMULA I where n = 0.
Table II below shows the various derivatives synthesised.

| R | Y—B Organic nitrates | | | |
|---|---|---|---|---|
| | isosorbide-ONO$_2$ | isomannide-ONO$_2$ | isoidide-NH | isosorbide-NH |
| CH$_3$—[thiazolidine]—N—COO—C(CH$_3$)$_3$ | 53 | | | |
| CH$_3$—[thiazolidine]—NH·HCl | | 54 | | |
| CH$_3$OOC—[thiazolidine]—N—COO—C(CH$_3$)$_3$ | | | 55 | |
| C$_6$H$_5$—[thiazolidine]—N—COO—C(CH$_3$)$_3$ | | | | 56 |

II — SYNTHESIS OF THE COMPOUNDS OF FORMULA I where n = 0.
Table II below shows the various derivatives synthesised.

EXAMPLE 18

2-O-[(3-t-Butoxycarbonyl-4-L-thiazolidinyl)carbonyl]-5-O-nitro-1,4:3,6-dianhydro-D-glucitol (18)

5 g (26.1 mmol) of 1,4:3,6-dianhydro-D-glucitol-5-nitrate, 6.15 g (26.3 mmol) of N-t-Boc-L-thioproline, 5.4 g (26.1 mmol) of DCC, 3.55 g (26.2 mmol) of HOBt and 0.435 g (2.9 mmol) of 4-pyrrolidinopyridine are stirred in 225 ml of dichloromethane (stabilised on amylene and dried over alumina) for 24 hours at ambient temperature. After filtering off DCU, the subsequent procedure is as for (1). The evaporation residue is chromatographed on silica (230–400 mesh ASTM) and the product isolated is recrystallised from ethyl acetate and then washed with petroleum ether. 5.5 g are obtained (Yield=51%).

m.p.=106°–110° C., $[\alpha]_D^{20}$=+10.6 (c 0.6 acetone).

Analysis

|  | C | H | N |
|---|---|---|---|
| Calc. | 44.33 | 5.45 | 6.89 |
| Found | 44.4 | 5.5 | 6.8 |

EXAMPLE 19

2-O-[(4-L-Thiazolidinyl)carbonyl]-5-O-nitro-1,4:3,6-dianhydro-D-glucitol monohydrochloride (19)

2.5 g (6.1 mmol) of the above product (18) are added to 32 ml of a 2N hydrochloric acid solution in ethyl acetate. The solution is stirred for 1 hour at ambient temperature and the precipitate formed is filtered off and then washed with ether. After recrystallisation from ethanol, 2.85 g of product are obtained (Yield=76%).

m.p.=183° C. (dec), $[\alpha]_D^{20}$=+42.8 (c 0.6 water).

Analysis

|  | C | H | N |
|---|---|---|---|
| Calc. | 35.04 | 4.41 | 8.17 |
| Found | 34.7 | 4.4 | 8.1 |

EXAMPLE 20

S-[(Acetylamino)methyl]-N-[(t-butoxy)carbonyl]-L-cysteine ester of 5-O-nitro-1,4:3,6-dianhydro-D-glucitol (20)

1.91 g (10 mmol) of 1,4:3,6-dianhydro-D-glucitol 5-nitrate, 3.5 g (12 mmol) of N-t-Boc-S-acetamidomethyl-L-cysteine (12 mmol), 2.47 g (12 mmol) of DCC, 1.6 g (12 mmol) of HOBt and 0.2 g (1.3 mmol) of 4-pyrrolidinopyridine are stirred in 100 ml of dichloromethane (stabilised on amylene and dried over alumina) for 6 hours. After filtering off DCU, the solution is washed and dried as for (1). The product isolated after chromatography is recrystallised from an acetone/isopropyl ether mixture (50-50). 3.4 g are obtained (Yield=73%).

m.p.=105°–106° C., $[\alpha]_D^{20}$=+59 (c 0.6 acetone).

Analysis

|  | C | H | N | O |
|---|---|---|---|---|
| Calc. | 43.87 | 5.85 | 9.03 | 34.37 |
| Found | 43.8 | 5.8 | 8.7 | 34.1 |

EXAMPLE 21

S-[(Acetylamino)methyl]-L-cysteine ester of 5-O-nitro-1,4:3,6-dianhydro-D-glucitol monohydrochloride (21)

2.9 g (6.2 mmol) of the above product (20) are added to 24 ml of a 2N hydrochloric acid solution in ethyl acetate. The solution is stirred for 5 hours at ambient temperature and the precipitate formed is filtered off and then washed with ether. After chromatography on silica (230–400 mesh ASTM), the product is recrystallised from an ethanol/acetone mixture. 2.15 g are obtained (Yield=85%).

m.p.=152°–155° C.

EXAMPLE 22

2-O-[2-[(Phenylmethyl)thio]benzoyl]-5-O-nitro-1,4:3,6-dianhydro-D-glucitol (22)

10.5 g (40 mmol) of S-benzyl-thiosalicilic acid chloride are dissolved in 100 ml of anhydrous pyridine and introduced into the reactor. A solution of 5.7 g (30 mmol) of 1,4:3,6-dianhydro-D-glucitol 5-nitrate in 50 ml of anhydrous pyridine is then run in dropwise at ambient temperature. The mixture is heated at 40° C., with stirring for 24 hours. The pyridine is evaporated without exceeding 40° C. and the residue is taken up in dichloromethane, washed with water, with 1N hydrochloric acid, with water, with an aqueous sodium bicarbonate solution and then with water until neutral and dried over sodium sulphate. The viscous product is then chromatographed on silica (230–400 mesh ASTM) and the compound isolated is recrystallised from an 80-20 diisopropyl ether/ethyl acetate mixture. 6.1 g of product are obtained (Yield=49%).

m.p.=98°–99° C.

Analysis

|  | C | H | N |
|---|---|---|---|
| Calc. | 57.55 | 4.59 | 3.35 |
| Found | 57.4 | 4.4 | 3.3 |

EXAMPLE 23

2-O-[2-[(Acetylamino)methyl]thio]benzoyl]-5-O-nitro-1,4:3,6-dianhydro-D-glucitol (23)

3.8 g (20 mmol) of 1,4:3,6-dianhydro-D-glucitol 5-nitrate, 5 g (22 mmol) of S-acetaminomethylthiosalicylic acid, 4.5 g (22 mmol) of DCC and 0.44 g (3 mmol) of 4-pyrrolidinopyridine are stirred for 48 hours at ambient temperature in 60 ml of dichloromethane (stabilised on amylene and dried over alumina). After filtering off DCU, the solution is washed and dried as for (1). The product isolated after chromatography is recrystallised from ethanol. 5.6 g are obtained (Yield=67%).

m.p.=126°–127° C., $[\alpha]_D^{20}$=+93.4 (c 0.5 acetone).

Analysis

|  | C | H | N | O |
| --- | --- | --- | --- | --- |
| Calc. | 48.23 | 4.56 | 7.04 | 32.14 |
| Found | 47.8 | 4.4 | 6.8 | 32.2 |

EXAMPLE 24

5-O-[(3-t-Butoxycarbonyl-4-L-thiazolidinyl)carbonyl]-2-O-nitro-1,4:3,6-dianhydro-D-glucitol (24)

6 g (31.4 mmol) of 1,4:3,6-dianhydro-D-glucitol 2-nitrate, 7.38 g (31.6 mmol) of N-t-Boc-L-thioproline, 6.48 g (31.4 mmol) of DCC, 4.26 g (31.5 mmol) of HOBt and 0.52 g (3.5 mmol) of 4-pyrrolidinopyridine are stirred in 270 ml of dichloromethane stabilised on amylene and dried over alumina) for 24 hours. After filtering off DCU, 200 ml of dichloromethane are added and the solution is washed and dried as for (1). The product isolated is recrystallised from an ethyl acetate/petroleum ether mixture. 7.6 g are obtained (Yield=60%).

m.p.=93° C., $[\alpha]_D^{20}$=−15.6 (c 0.6 ethanol).
Analysis

|  | C | H | N |
| --- | --- | --- | --- |
| Calc. (0.15 H$_2$O) | 44.03 | 5.48 | 6.84 |
| Found | 44.0 | 5.4 | 6.8 |

EXAMPLE 25

5-O-[(4-L-Thiazolidinyl)carbonyl]-2-O-nitro-1,4:3,6-dianhydro-D-glucitol monohydrochloride (25)

6.8 g of the above compound (24) are added to 65 ml of a 2N hydrochloric acid solution in ethyl acetate. The solution is stirred for 1 hour at ambient temperature and the precipitate formed is filtered off and washed with ether before being recrystallised from methanol. 2.35 g are obtained (Yield=40%).

m.p.=175° C. (dec), $[\alpha]_D^{20}$=+15.8 (c 0.6 water).
Analysis

|  | C | H | N |
| --- | --- | --- | --- |
| Calc. (0.15 H$_2$O) | 34.75 | 4.45 | 8.10 |
| Found | 34.7 | 4.4 | 7.9 |

EXAMPLE 26

S-[(Acetylamino)methyl]-N-[(t-butoxy)carbonyl]-L-cysteine ester of 2-O-nitro-1,4:3,6-dianhydro-D-glucitol (26)

3.5 g (18 mmol) of 1,4:3,6-dianhydro-D-glucitol 2-nitrate, 5.3 g (18 mmol) of N-t-Boc-S-acetamidomethyl-L-cysteine, 3.78 g (18 mmol) of DCC, 2.43 g (18 mmol) of HOBt and 0.3 g (2 mmol) of 4-pyrrolidinopyridine are stirred in 150 ml of dichloromethane (stabilised on amylene and dried over alumina) for 24 hours. After filtering off DCU, 250 ml of dichloromethane are added and the solution is washed and dried as for (1). The product isolated is recrystallised from an acetone/diisopropyl ether mixture (40-60). 3.95 g are obtained (Yield=46%).

m.p.=115° C. (dec), $[\alpha]_D^{20}$=+11.2 (c 0.6 ethanol).
Analysis

|  | C | H | N |
| --- | --- | --- | --- |
| Calc. | 43.86 | 5.84 | 9.02 |
| Found | 43.8 | 5.9 | 9.0 |

EXAMPLE 27

S-[(Acetylamino)methyl]-L-cysteine ester of 2-O-nitro-1,4:3,6-dianhydro-D-glucitol monohydrochloride (27)

2.3 g of the above compound (26) are added to 21 ml of a 2N hydrochloric acid solution in ethyl acetate. The solution is stirred for 1 hour at ambient temperature and the precipitate formed is filtered off and washed with ether before being recrystallised from ethanol. 1.75 g are obtained (Yield=88%). m.p.=161°–162° C., $[\alpha]_D^{20}$=+31.6 (c 0.6 water).
Analysis

|  | C | H | N |
| --- | --- | --- | --- |
| Calc. | 35.86 | 5.01 | 10.45 |
| Found | 35.4 | 4.9 | 10.3 |

EXAMPLE 28

5-O-[2-[(Phenylmethyl)thio]benzoyl]-2-O-nitro-1,4:3,6-dianhydro-D-glucitol (28)

7.8 g (30 mmol) of S-benzyl-thiosalicylic acid chloride are dissolved in 65 ml of anhydrous pyridine and introduced into the reactor. A solution of 4 g (21 mmol) of 1,4:3,6-dianhydro-D-glucitol 2-nitrate in 35 ml of anhydrous pyridine is then run in dropwise at 40° C. The reaction is allowed to proceed for 24 hours, with stirring. The subsequent treatment is then as for (22). The product is recrystallised from a methanol/acetone mixture (40-20). 4.4 g of product are obtained (Yield=51%).

m.p.=105°–106° C., $[\alpha]_D^{20}$=+77.2 (c 2, acetone).
Analysis

|  | C | H | N |
| --- | --- | --- | --- |
| Calc. | 57.55 | 4.59 | 3.35 |
| Found | 57.5 | 4.5 | 3.3 |

EXAMPLE 29

Bis[5-O-[(2-thio)benzoyl]-2-O-nitro-1,4:3,6-dianhydro-D-glucitol] (29)

13.5 g (60 mmol) of acetamidomethylthiosalicylic acid are stirred with 50 ml of thionyl chloride for 1 hour at 70° C. and the excess thionyl chloride is evaporated under vacuum without exceeding 50° C. After cooling, 60 ml of dry pyridine are added, which causes vigorous effervescence and a rise in temperature. The black solution is recovered by settling and a solution of 3.8 g (20 mmol) of 1,4:3,6- dianhydro-D-glucitol 2-nitrate in 10 ml of pyridine is added dropwise thereto. The mixture is stirred for 30 hours at 40° C. and the pyridine is evaporated under vacuum. The residue is taken up in dichloromethane, the mixture is filtered through silica and the solution is washed and dried as for (1). The product recovered is chromatographed on a silica column. 3.5 g of product are isolated, which product is recrystallised from an acetone/ethanol mixture (1-2). 1.8 g of product are obtained (Yield=34%).

m.p.=140°–142° C., $[\alpha]_D^{20}$=+79.2 (c 0.5 acetone).

Analysis

|       | C     | H    | O     | N    | S    |
|-------|-------|------|-------|------|------|
| Calc. | 47.85 | 3.71 | 34.32 | 4.29 | 9.83 |
| Found | 47.8  | 3.3  | 34.3  | 4.0  | 9.6  |

EXAMPLE 30

5-[[(4-L-Thiazolidinyl)carbonyl]amino]-5-deoxy-2-O-nitro-1,4:3,6-dianhydro-L-iditol monohydrochloride (30)

*Method A:

A solution of 3.2 g (16.85 mmol) of 5-amino-1,4:3,6-dianhydro-5-deoxy-L-iditol 2-nitrate in 120 ml of anhydrous dichloromethane is stirred at 0° C. 1.87 g (14.05 mmol) of L-thioproline, 2.9 g (14.05 mmol) of DCC and 1.9 g (14.05 mmol) of HOBt are added successively. After 3 hours at this temperature, stirring is continued for a further 20 hours at ambient temperature. After filtering off DCU and evaporation of the solvent, the oil is chromatographed on silica (230–400 mesh ASTM). The oil isolated is dissolved in dichloromethane and hydrogen chloride is bubbled through the solution. After evaporation of the solvent, the residue is crystallised with methanol and then recrystallised from this solvent. 2.6 g are obtained (Yield=54%).

*Method B:

A solution of 5 g (26.3 mmols) of 5-amino-1,4:3,6-dianhydro-5-deoxy-L-iditol 2-nitrate in 300 ml of anhydrous dichloromethane is stirred at ambient temperature. 6.13 g (26.3 mmols) of N-t-Boc-L-thioproline, 5.43 g (26.3 mmols) of DCC and 3.55 g (26.3 mmols) of HOBt are added successively. After a reaction time of 24 hours and filtering off the DCU, 200 ml of dichloromethane are added and the washings are carried out as for (1). The evaporation residue is chromatographed on silica (230–400 mesh ASTM) and 10.5 g of an oil corresponding to 5-[[(3-t-butoxycarbonyl-4-L-thiazolidinyl)carbonyl]amino]-5-deoxy-2-O-nitro-1,4:3,6-dianhydro-L-iditol (50) are isolated. The latter was not crystallised: it is treated directly.

The 10.5 g of the above compound are added to 80 ml of a 2N solution of hydrochloric acid in ethyl acetate. The solution is stirred for 3 hours at ambient temperature and the white solid formed is filtered off and then washed with ether. After recrystallisation from methanol, 7.35 g of product (30) are obtained (yield=81%).

m.p.=185°–199° C. (dec), $[\alpha]_D^{20}$=–60.7 (c 2, water).

Analysis

|       | C     | H    | N     | Cl    |
|-------|-------|------|-------|-------|
| Calc. | 35.14 | 4.72 | 12.30 | 10.37 |
| Found | 35.1  | 4.5  | 12.1  | 10.4  |

EXAMPLE 31

5-[[(3-Formyl-2,2-dimethyl-4-L-thiazolidinyl)carbonyl]amino]-5-deoxy-2-O-nitro-1,4:3,6-dianhydro-L-iditol monohydrochloride (31)

A solution of 2.94 g (15.5 mmol) of 5-amino-1,4:3,6-dianhydro-5-deoxy-L-iditol 2-nitrate in 150 ml of anhydrous dichloromethane is stirred at ambient temperature. 2.95 g (15.5 mmol) of N-formyl-L-dimethylthioproline, 3.20 g (15.5 mmol) of DCC and 2.1 g (15.5 mmol) of HOBt are added successively. After a reaction time of 24 hours, DCU is filtered off, the solvent is evaporated and the solid obtained is chromatographed (on silica, 230–400 mesh ASTM). After recrystallisation from methanol, 3.05 g of white solid are obtained (Yield=54%).

m.p.=158° C., $[\alpha]_D^{20}$=–59 (c 0.6 acetone).

Analysis

|       | C     | H    | N     |
|-------|-------|------|-------|
| Calc. | 43.20 | 5.30 | 11.63 |
| Found | 43.0  | 5.3  | 11.7  |

EXAMPLE 32

5-[[(2,2-Dimethyl-4-L-thiazolidinyl)carbonyl]amino]-5-deoxy-2-O-nitro-1,4:3,6-dianhydro-L-iditol monohydrochloride (32)

A solution of 3 g (15.8 mmol) of 5-amino-1,4:3,6-dianhydro-5-deoxy-L-iditol 2-nitrate in 130 ml of anhydrous dichloromethane is stirred at ambient temperature. 3.07 g (15.5 mmol) of L-dimethylthioproline, 3.26 g (15.7 mmol) of DCC and 2.14 g (15.7 mmol) of HOBt are added successively. After a reaction time of 24 hours, DCU is filtered off, the solvent is evaporated and the oily residue is chromatographed on silica (230–400 mesh ASTM). The subsequent procedure is then as for (30) and 2.7 g of product recrystallised from methanol are obtained (Yield=47%).

m.p.=196° C. (dec), $[\alpha]_D^{20}$=from –12 to +17 (c 0.6 water); a variation due to the instability of the product in water; it converts to:

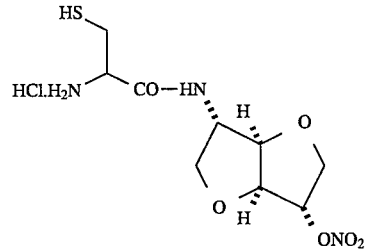

which itself changes to the oxidised form (cystine).

Analysis

|       | C     | H    | N     | Cl   |
|-------|-------|------|-------|------|
| Calc. | 38.97 | 5.45 | 11.36 | 9.58 |
| Found | 38.5  | 5.4  | 11.1  | 9.5  |

EXAMPLE 33

S-[(Acetylamino)methyl]-N-[(t-butoxy)carbonyl]-
L-cysteine amide of
5-amino-5-deoxy-2-O-nitro-1,4:3,6-dianhydro-L-iditol
(33)

A solution of 2.56 g (13.5 mmol) of 5-amino-1,4:3,6-dianhydro-5-deoxy-L-iditol 2-nitrate in 120 ml of anhydrous dichloromethane is stirred at ambient temperature. 3.95 g (13.5 mmol) of N-t-Boc-S-acetamidomethyl-L-cysteine, 2.8 g (13.5 mmol) of DCC and 1.82 g (13.5 mmol) of HOBt are added successively. After reaction for 24 hours, filtering off DCU and evaporating the solvent, the pasty compound isolated is chromatographed on silica (230–400 mesh ASTM). The solid obtained is recrystallised from ethyl acetate. 5.9 g are obtained (Yield=94%).

m.p.=152° C., $[\alpha]_D^{20}$=+26.1 (c 0.6 acetone).

Analysis

|       | C     | H    | N     |
|-------|-------|------|-------|
| Calc. | 43.96 | 6.07 | 12.06 |
| Found | 44.1  | 6.0  | 12.0  |

EXAMPLE 34

S-[(Acetylamino)methyl]-L-cysteine amide of
5-amino-5-deoxy-2-O-nitro-1,4:3,6-dianhydro-L-iditol
monohydrochloride (34)

2 g of the above compound (33) are added to 13 ml of a 1.6N hydrochloric acid solution in methanol. The solution is stirred for 24 hours at ambient temperature and the white solid is filtered off. The solvent is evaporated from the filtrate and the viscous compound obtained is chromatographed (silica, 230–400 mesh ASTM). The oil isolated is crystallised with pyridine and acetone and the solid is recrystallised from an ethanol/acetone mixture and then from ethanol. 0.95 g is obtained (Yield=55%). m.p.=183° C., $[\alpha]_D^{20}$=+28.3 (c 0.6 water).

Analysis

|                              | C     | H    | N     |
|------------------------------|-------|------|-------|
| Calc. (0.15 H$_2$O)          | 35.71 | 5.31 | 13.88 |
| Found                        | 35.7  | 5.3  | 13.7  |

EXAMPLE 35

S-[(2-Nitrophenyl)thio]-N-[(t-butoxy)carbonyl]-
L-cysteine amide of
5-amino-5-deoxy-2-O-nitro-1,4:3,6-dianhydro-L-iditol
(35)

A solution of 1 g (5.2 mmol) of 2-nitrobenzenesulfenyl chloride is run into a solution of 2 g (4.3 mmol) of (33) in 12 ml of anhydrous acetic acid, at ambient temperature and with stirring. After a reaction time of 2 hours 30, the acetic acid is evaporated under vacuum. The oil obtained is crystallised from ether and the product is then chromatographed on silica (230–400 mesh ASTM). The solid isolated is recrystallised from methanol. 1.1 g are obtained (Yield=38%).

m.p.=157°–158° C., $[\alpha]_D^{20}$=+5.33 (c 0.6 acetone).

Analysis

|       | C     | H    | N     |
|-------|-------|------|-------|
| Calc. | 43.95 | 4.79 | 10.25 |
| Found | 43.9  | 4.7  | 10.2  |

Under the reaction conditions a by-product is obtained in a significant amount; it corresponds to the salt of the amine (36) formed after the t-butoxycarbonyl group has left.

EXAMPLE 36

N-[(t-Butoxy)carbonyl]-L-methionine amide of
5-amino-5-deoxy-2-O-nitro-1,4:3,6-dianhydro-L-iditol
(37)

A solution of 3.85 g (22 mmol) of 5-amino-1,4:3,6-dianhydro-5-deoxy-L-iditol 2-nitrate in 190 ml of anhydrous dichloromethane is stirred at room temperature. 5 g (20 mmol) of N-t-Boc-L-methionine, 4.15 g (21 mmol) of DCC and 2.7 g (21 mmol) of HOBt are added successively. After a reaction time of 24 hours, DCU is filtered off, the solvent is evaporated and the oil obtained is chromatographed (silica, 230–400 mesh ASTM). The compound isolated is recrystallised from an ethyl acetate/diisopropyl ether mixture (1-2). 4.7 g are obtained (Yield=55%).

m.p.=96° C.

Treatment of this compound with a 1.7N hydrochloric acid solution in methanol enables the t-butoxycarbonyl group to be removed and leads to the hydrochloride of the corresponding amine (38).

EXAMPLE 37

5-[[2-[(Phenylmethyl)thio]benzoyl]amino-5-deoxy-2-
O-nitro-1,4:3,6-dianhydro-L-iditol (39)

A solution of 3 g (15.8 mmol) of 5-amino-1,4:3,6-dianhydro-5-deoxy-L-iditol 2-nitrate in 130 ml of anhydrous dichloromethane is stirred at ambient temperature. 3.2 g (13.1 mmol) of S-benzylthiosalicylic acid and 2.75 g (13.3 mmol) of DCC are added successively. After a reaction time of 24 hours, DCU is filtered off, the solvent is evaporated and the oil obtained is chromatographed (silica, 230–400 mesh ASTM). After recrystallisation from an acetone/hexane mixture, 2.55 g are obtained (Yield=47%).

m.p.=87°–88° C., $[\alpha]_D^{20}$=+29.3 (c 2 acetone).

Analysis

|       | C     | H    | N    |
|-------|-------|------|------|
| Calc. | 57.68 | 4.84 | 6.72 |
| Found | 57.6  | 5.0  | 6.7  |

EXAMPLE 38

2-[[(4-L-Thiazolidinyl)carbonyl]amino]-2-deoxy-5-
O-nitro-1,4:3,6-dianhydro-D-glucitol
monohydrochloride (40)

A solution of 4.45 g (23.4 mmol) of 2-amino-1,4:3,6-dianhydro-2-deoxy-D-glucitol 5-nitrate in 200 ml of anhydrous dichloromethane is stirred at ambient temperature. 3.1 g (23.3 mmol) of L-thioproline, 4.8 g (23.3 mmol) of DCC and 3.15 g (23.3 mmol) of HOBt are added successively.

After a reaction time of 24 hours, DCU is filtered off, the solvent is evaporated and the compound obtained is chromatographed (silica, 230–400 mesh ASTM). The subsequent procedure is then as for (30) and the hydrochloride obtained is recrystallised from methanol. 2.3 g are isolated (Yield=29%).

m.p.=187°–188° C. (dec), $[\alpha]_D^{20}$=+11.8 (c 0.6 water).

Analysis

|  | C | H | N | S | Cl |
|---|---|---|---|---|---|
| Calc. | 35.14 | 4.72 | 12.30 | 9.38 | 10.37 |
| Found | 35.2 | 4.7 | 11.7 | 9.2 | 10.3 |

EXAMPLE 39

S-[(Acetylamino)methyl]-N-[(t-butoxy)carbonyl]-L-cysteine amide of 2-amino-2-deoxy-5-O-nitro-1,4:3,6-dianhydro-D-glucitol (41)

A solution of 4.15 g (21.8 mmol) of 2-amino-1,4:3,6-dianhydro-2-deoxy-D-glucitol 5-nitrate in 200 ml of anhydrous dichloromethane is stirred at ambient temperature. 6.4 g (21.8 mmol) of N-t-Boc-S-acetamidomethyl-L-cysteine, 4.53 g (21.9 mmol) of DCC and 2.95 g (21.8 mmol) of HOBt are added successively. After reaction for 24 hours, filtering off DCU and evaporating the solvent, the product is chromatographed on silica (230–400 mesh ASTM). The compound isolated is recrystallised from ethyl acetate; 4.5 g are obtained (Yield=44%).

m.p.=90°–92° C., $[\alpha]_D^{20}$=+78.1 (c 0.6 ethanol).

Analysis

|  | C | H | N | O |
|---|---|---|---|---|
| Calc. (0.6 H$_2$O) | 42.96 | 6.18 | 11.78 | 32.31 |
| Found | 42.9 | 6.2 | 11.7 | 32.4 |

EXAMPLE 40

S-[(Acetylamino)methyl]-L-cysteine amide of 2-amino-2-deoxy-5-O-nitro-1,4:3,6-dianhydro-D-glucitol monohydrochloride (42)

4.3 g of the above compound (41) are added to 23 ml of a 2.2N hydrochloric acid solution in methanol. The mixture is stirred for 18 hours at ambient temperature and the solution is concentrated before being chromatographed on silica (230–400 mesh ASTM). The compound isolated is recrystallised from ethanol; 3.1 g are obtained (Yield=83%).

m.p.=94°–95° C., $[\alpha]_D^{20}$=+74.8 (C 0.6 water).

Analysis

|  | C | H | N | Cl |
|---|---|---|---|---|
| Calc. (0.8 H$_2$O) | 34.71 | 5.23 | 13.49 | 8.53 |
| Found | 34.7 | 5.4 | 13.3 | 8.6 |

EXAMPLE 41

N-[(t-Butoxy)carbonyl]-L-methionine amide of 2-amino-2-deoxy-5-O-nitro-1,4:3,6-dianhydro-D-glucitol (43)

A solution of 3.26 g (18 mmol) of 2-amino-1,4:3,6-dianhydro-2-deoxy-D-glucitol 5-nitrate in 170 ml of anhydrous dichloromethane is stirred at ambient temperature. 4.5 g (18 mmol) of N-t-Boc-L-methionine, 7.65 g (18 mmol) of CMC and 2.42 g (18 mmol) of HOBt are added successively. After a reaction time of 24 hours, dichloromethane is added and the subsequent procedure is as for the preparation of (1). 5.4 g of a solid are isolated, which solid is recrystallised from an ethanol/diisopropyl ether mixture (1-4). 2.55 g are obtained (Yield=34%).

m.p.=114° C., $[\alpha]_D^{20}$=+67.6 (c 0.6 ethanol).

Analysis

|  | C | H | N |
|---|---|---|---|
| Calc. | 45.59 | 6.45 | 9.96 |
| Found | 45.3 | 6.3 | 9.8 |

Treatment of this compound with a 1.7N hydrochloric acid solution in methanol leads to the corresponding hydrochloride (44).

EXAMPLE 42

2-[[2-[(Phenylmethyl)thio]benzoyl]amino-2-deoxy-5-O-nitro-1,4:3,6-dianhydro-D-glucitol (45)

A solution of 3.5 g (18.4 mmol) of 2-amino-1,4:3,6-dianhydro-2-deoxy-D-glucitol 5-nitrate in 160 ml of anhydrous dichloromethane is stirred at ambient temperature. 4.5 g (18.4 mmol) of S-benzylthiosalicylic acid and 3.8 g (18.4 mmol) of DCC are added successively. After reaction for 24 hours, filtering off DCU and evaporation of the solvent, the residue is chromatographed on silica (230–400 mesh ASTM) and the compound isolated is recrystallised from an ethyl acetate/diisopropyl ether mixture. 2.2 g are obtained (Yield=36%).

m.p.=86°–90° C., $[\alpha]_D^{20}$=+64.8 (c 0.6 ethanol).

Analysis

|  | C | H | N |
|---|---|---|---|
| Calc. | 57.68 | 4.84 | 6.72 |
| Found | 57.7 | 4.8 | 6.6 |

EXAMPLE 43

5-[[(3-acetyl-4-L-thiazolidinyl)carbonyl]amino]-5-deoxy-2-O-nitro-1,4:3,6-dianhydro-L-iditol (51)

A solution of 2 g (10.5 mmols) of 5-amino-1,4:3,6-dianhydro-5-deoxy-L-iditol 2-nitrate in 80 ml of anhydrous dichloromethane is stirred at ambient temperature. 1.84 g (10.5 mmols) of N-acetyl-L-thioproline, 4.45 g (10.5 mmols) of CMC and 1.42 g (10.5 mmols) of HOBt are added successively. After a reaction time of 24 hours, 50 ml of dichloromethane are added and the washings are carried out as for (1). After drying the organic phase over sodium sulphate, filtering off and evaporating the solvent, the solid obtained is recrystallised from ethyl acetate. 1.6 g of product are obtained (yield=44%).

m.p.=169° C., $[\alpha]_D^{20}$=−62.0 (c 1, ethanol).

Analysis

|  | C | H | N |
|---|---|---|---|
| Calc. | 41.50 | 4.93 | 12.10 |
| Found | 41.4 | 4.9 | 12.1 |

EXAMPLE 44

5-[[(3-benzoyl-4-L-thiazolidinyl)carbonyl]amino]-5-deoxy-2-O-nitro-1,4:3,6-dianhydro-L-iditol (52)

A solution of 2 g (10.5 mmols) of 5-amino-1,4:3,6-dianhydro-5-deoxy-L-iditol 2-nitrate in 100 ml of anhydrous dichloromethane is stirred at ambient temperature. 2.5 g (10.5 mmols) of N-benzoyl-L-thioproline, 2.16 g (10.5 mmols) of DCC and 1.42 g (10.5 mmols) of HOBt are added successively. After a reaction time of 24 hours, the DCU is filtered off, 100 ml of dichloromethane are added and the washings are carried out as for (1). The residue obtained after evaporation is chromatographed on silica (230–400 mesh ASTM) and the product isolated is recrystallised from methanol; 2.04 g of compound are obtained (yield=40%).

m.p.=166°–167° C., $[\alpha]_D^{20}$=−106.9 (c 1, DSMO).

Analysis

|  | C | H | N |
|---|---|---|---|
| Calc. | 49.87 | 4.68 | 10.26 |
| Found | 49.7 | 4.6 | 10.2 |

EXAMPLE 45

5-[[(3-t-butoxycarbonyl-2-methyl-4-L-thiazolidinyl)carbonyl]amino]-5-deoxy-2-O-nitro-1,4:3,6-dianhydro-L-iditol A solution of 3 g (15.7 mmols) of 5-amino-1,4:3,6-dianhydro-5-deoxy-L-iditol 2-nitrate in 120 ml of anhydrous dichloromethane is stirred at ambient temperature. 3.9 g (15.7 mmol) of N-t-Boc-2-methyl-L-thioproline, 3.26 g (15.7 mmols) of DCC and 2.13 g (15.7 mmols) of HOBt are added successively. After a reaction time of 24 hours and filtering off the DCU, 80 ml of dichloromethane are added and the washings are carried out as for (1). The residue obtained after evaporation is chromatographed on silica (230–400 mesh ASTM). 5.6 g of a white solid are isolated and the latter is recrystallised from ethyl acetate. 4.17 g of product are obtained (yield=63%). NMR indicates a single configuration for the carbon in the 2-position.

m.p.=129°–130° C., $[\alpha]_D^{20}$=−18.8 (c 1, ethanol).

Analysis

|  | C | H | N |
|---|---|---|---|
| Calc. | 45.82 | 6.01 | 10.02 |
| Found | 45.7 | 6.0 | 10.0 |

EXAMPLE 46

5-[[(2-methyl-4-L-thiazolidinyl)carbonyl]amino]-5-deoxy-2-O-nitro-1,4:3,6-dianhydro-L-iditol monohydrochloride (54)

4.09 g of the above compound are added to 34 ml of a 2N solution of hydrochloric acid in ethyl acetate. The solution is stirred for 16 hours at ambient temperature and the white solid formed is filtered and then washed with ether. After recrystallisation from methanol, 2.58 g of product are obtained (yield=74%). NMR shows that it corresponds to a mixture of two diastereoisomers in the 2-position.

m.p.=209° C. (dec) , $[\alpha]_D^{20}$=−55.1 (c 1, water).

Analysis

|  | C | H | N | Cl |
|---|---|---|---|---|
| Calc. | 37.13 | 5.10 | 11.81 | 9.96 |
| Found | 37.2 | 5.1 | 11.8 | 9.9 |

EXAMPLE 47

5-[[(3-t-butoxycarbonyl-2-methoxycarbonyl-4-L-thiazolidinyl)carbonyl]amino]-5-deoxy-2-O-nitro-1,4:3,6-dianhydro-L-iditol (55)

A solution of 1.73 g (9.1 mmols) of 5-amino-1,4:3,6-dianhydro-5-deoxy-L-iditol 2-nitrate in 50 ml of anhydrous dichloromethane is stirred at ambient temperature. 2.66 g (9.1 mmols) of N-t-Boc-2-methoxycarbonyl-L-thioproline, 1.89 g (9.1 mmols) of DCC and 1.23 g (9.1 mmols) of HOBt are added successively. After a reaction time of 24 hours and filtering off the DCU, 50 ml of dichloromethane are added and the washings are carried out as for (1). The oily residue obtained after evaporation is chromatographed on silica (230–400 mesh ASTM). 2.44 g of a white solid are isolated and the latter is recrystallised from methanol. 2.04 g of product are obtained (yield=48%). NMR indicates a single configuration for the carbon in the 2-position.

m.p.=132°–133° C., $[\alpha]_D^{20}$=−13.9 (c 1, ethanol).

Analysis

|  | C | H | N |
|---|---|---|---|
| Calc. | 44.06 | 5.44 | 9.07 |
| Found | 44.2 | 5.6 | 9.2 |

EXAMPLE 48

5-[[(3-t-butoxycarbonyl-2-phenyl-4-L-thiazolidinyl)carbonyl]amino]-5-deoxy-2-O-nitro-1,4:3,6-dianhydro-L-iditol (56)

A solution of 5 g (26.29 mmols) of 5-amino-1,4:3,6-dianhydro-5-deoxy-L-iditol 2-nitrate in 200 ml of anhydrous dichloromethane is stirred at ambient temperature. 8.1 g (26.29 mmols) of N-t-Boc-2-phenyl-L-thioproline, 5.4 g (26.29 mmols) of DCC and 3.6 g (26.29 mmols) of HOBt are added successively. After a reaction time of 24 hours and filtering off the DCU, 100 ml of dichloromethane are added and the washings are carried out as for (1). The oily residue obtained after evaporation is chromatographed on silica (230–400 mesh ASTM). 10.7 g of a white solid are isolated and the latter is recrystallised from ethyl acetate. 9.3 g of product are obtained (yield=73%). NMR indicates a single configuration for the carbon in the 2-position.

m.p.=115° C., $[\alpha]_D^{20}$=+87.5 (c 1, ethanol).

Analysis

|  | C | H | N |
|---|---|---|---|
| Calc. (0.5 H$_2$O) | 51.42 | 5.74 | 8.56 |
| Found | 51.3 | 5.6 | 8.6 |

EXAMPLE 49

5-[[(2-phenyl-4-L-thiazolidinyl)carbonyl]amino]-5-deoxy-2-O-nitro-1,4:3,6-dianhydro-L-iditol monohydrochloride (57)

2 g of the above compound are added to 15 ml of a 2N solution of hydrochloric acid in ethyl acetate. The solution is stirred for 16 hours at ambient temperature and, after evaporation of the solvent, 1.66 g of a white solid are recovered. After recrystallisation from methanol, 0.95 g of product is obtained (yield=50%). NMR shows that it corresponds to a mixture of two diastereoisomers in the 2-position.

m.p.=197° C. (dec), $[\alpha]_D^{20}$=−38.1 (c 1, DMSO).

Analysis

|  | C | H | N | Cl |
|---|---|---|---|---|
| Calc. (0.6 H$_2$O) | 44.83 | 4.98 | 9.80 | 8.27 |
| Found | 44.5 | 4.7 | 9.6 | 8.4 |

EXAMPLE 50

5-[[(3-t-butoxycarbonyl-2-butyl-4-L-thiazolidinyl)carbonyl]amino]-5-deoxy-2-O-nitro-1,4:3,6-dianhydro-L-iditol A solution of 4 g (21 mmols) of 5-amino-1,4:3,6-dianhydro-5-deoxy-L-iditol 2-nitrate in 100 ml of anhydrous dichloromethane is stirred at ambient temperature. 6.08 g (21 mmols) of N-t-Boc-2-butyl-L-thioproline, 4.34 g (21 mmols) of DCC and 2.84 g (21 mmols) of HOBt are added successively. After a reaction time of 24 hours and filtering off the DCU, 120 ml of dichloromethane are added and the washings are carried out as for (1). The oily residue obtained after evaporation is chromatographed on silica (230–400 mesh ASTM). 7.8 g of a white solid are isolated and the latter is recrystallised from a mixture of ethyl acetate and petroleum ether. 4.76 g of product are obtained (yield=49%). NMR indicates a single configuration for the carbon in the 2-position.

m.p.=91°–92° C., $[\alpha]_D^{20}$=+4.3 (c 1, ethanol).

Analysis

|  | C | H | N |
|---|---|---|---|
| Calc. | 49.44 | 6.77 | 9.11 |
| Found | 49.7 | 6.7 | 9.1 |

EXAMPLE 51

5-[[(2-butyl-4-L-thiazolidinyl)carbonyl]amino]-5-deoxy-2-O-nitro-1,4:3,6-dianhydro-n-iditol monohydrochloride (59)

3.8 g of the above compound are added to 28 ml of a 2N solution of hydrochloric acid in ethyl acetate. The solution is stirred for 16 hours at ambient temperature and the white solid formed is filtered off and then washed with ether. After recrystallisation from methanol, 2.33 g of product are obtained (yield=71%). NMR shows that it corresponds to a mixture of two diastereoisomers in the 2-position.

m.p.=198°–200° C. (dec), $[\alpha]_D^{20}$=−34.2 (C 1, DMSO).

Analysis

|  | C | H | N | Cl |
|---|---|---|---|---|
| Calc. | 42.31 | 6.09 | 10.58 | 8.81 |
| Found | 42.1 | 6.0 | 10.4 | 8.6 |

III—SYNTHESIS OF COMPOUNDS OF FORMULA I where n=1.

III-a: R—CO+A—Y—B:

Table III below shows the various derivatives synthesised.

TABLE III

| A—Y—B | R | | | | |
|---|---|---|---|---|---|
| | BOC-thiazolidine | HCl·H-thiazolidine | CH₃-CO-thiazolidine | C₆H₅-CO-thiazolidine | S-CH₂-C₆H₅ phenyl |
| —HN—CH₂—CO—HN— (isosorbide-ONO₂) | 60 | 46 | 75 | 76 | 47 |
| —HN—CH—CO—HN— / CH₃ (isosorbide-ONO₂) | 61 | 62 | | | |
| —HN—CH—CO—HN— / CH(CH₃)₂ (isosorbide-ONO₂) | 63 | 64 | | | |
| —HN—CH—CO—HN— / CH₂C₆H₅ (isosorbide-ONO₂) | 65 | 66 | | | |

TABLE III-continued

| A—Y—B | R | | | | |
|---|---|---|---|---|---|
| -HN-CH-CO-HN-[sugar-ONO2]<br>CH2<br>CH2-S-CH3 | [pyrrolidine-S]-BOC<br>67 | [pyrrolidine-S]-HCl.H<br>68 | [pyrrolidine-S]-CH3-CO | [pyrrolidine-S]-C6H5-CO | [S-CH2-C6H5 on tolyl] |
| -CO-HN-[sugar-ONO2]<br>[pyrrolidine] | 69 | 70 | | | |
| -HN-CH2-CO-HN-[sugar-ONO2] | | 71 | | | |
| -HN-CH2-CO-O-[sugar-ONO2] | 72 | 73 | | | |

EXAMPLE 52

5-[[2-[(3-t-butoxycarbonyl-4-L-thiazolidinyl)carbonyl]amino]-1-oxoethyl]amino]-5-deoxy-Z-O-nitro-1,4:3,6-dianhydro-L-iditol (60)

A solution of 1 g (4.05 mmols) of the base form corresponding to (6) in 35 ml of anhydrous dichloromethane is stirred at ambient temperature. 0.94 g (4.05 mmols) of N-t-Boc-L-thioproline, 0.83 g (4.05 mmols) of DCC and 0.55 g (4.05 mmols) of HOBt are added successively. After a reaction time of 24 hours, the DCU is filtered off and the solvent is evaporated. The oil is chromatographed on silica (230–400 mesh ASTM) and 1.8 g of an oil which crystallises are isolated. The solid obtained is recrystallised from the ethyl acetate/diisopropyl ether mixture and then washed with petroleum ether. 1.33 g of product are obtained (yield=71%).

m.p.=127°–129° C., $[\alpha]_D^{20}$=–38.3 (c 0.6, ethanol).

Analysis

|       | C     | H    | N     |
|-------|-------|------|-------|
| Calc. | 44.15 | 5.66 | 12.11 |
| Found | 43.8  | 5.6  | 12.0  |

EXAMPLE 53

5-[[2-[[(4-L-Thiazolidinyl)carbonyl]amino]-1oxoethyl]amino]-5-deoxy-2-O-nitro-1,4:3,6-dianhydro-L-iditol monohydrochloride (46)

*Method A:

18 g of the above compound (60) are added to 132 ml of a 2N solution of hydrochloric acid in ethyl acetate. The solution is stirred for 16 hours at ambient temperature and the white solid formed is filtered off and then washed with ether; by concentrating the mother liquors, a second amount of product is recovered, which is added to the above product. After recrystallisation from methanol, 11.9 g of product are obtained (yield=76%).

m.p.=183°–188° C. (dec), $[\alpha]_D^{20}$=–46.9 (c 1, water).

Analysis

|       | C     | H    | N     |
|-------|-------|------|-------|
| Calc. | 36.14 | 4.80 | 14.04 |
| Found | 36.1  | 4.8  | 14.1  |

*Method B:

A solution of 2 g (8.09 mmol) of the base form corresponding to (6) in 70 ml of anhydrous dichloromethane is stirred at ambient temperature. 1.07 g (8 mmol) of L-thioproline, 1.65 g (8 mmol) of DCC and 1.09 g (8 mmol) of HOBt are added successively. After a reaction time of 24 hours, DCU is filtered off and the solvent is evaporated. The oil is chromatographed on silica (230–400 mesh ASTM) and a compound is isolated which is converted to its hydrochloride as for (30); the solid is refluxed in ethyl acetate, filtered off and recrystallised from methanol. 2.15 g are obtained (Yield=67%).

m.p.=183° C. (dec), $[\alpha]_D^{20}$=–46.9 (c 1 water).

Analysis

|       | C     | H    | N     |
|-------|-------|------|-------|
| Calc. | 36.14 | 4.80 | 14.04 |
| Found | 36.0  | 4.8  | 13.9  |

EXAMPLE 54

5-[[2-[[(3-t-butoxycarbonyl-4-n-thiazolidinyl)carbonyl]amino]-1-((2S)-2-methyl)-oxoethyl]amino]-5-deoxy-2-O-nitro-1,4:3,6-dianhydro-L-iditol (61)

A solution of 5 g (19.1 mmols) of the base form corresponding to (8) in 190 ml of anhydrous dichloromethane is stirred at ambient temperature. 4.5 g (19.1 mmols) of N-t-Boc-L-thioproline, 4.0 g (19.1 mmols) of DCC and 2.6 g (19.1 mmols) of HOBt are added successively. After a reaction time of 24 hours, the DCU is filtered off and the solvent is evaporated. The oil is chromatographed on silica (230–400 mesh ASTM) and an oil is isolated which is dissolved hot in ethyl acetate; the residual DCU is crystallised in this way. Diisopropyl ether is added to the filtrate, which enables 6.5 g of the expected compound to be recovered. The solid thus obtained is recrystallised twice from the ethyl acetate/diisopropyl ether mixture. 4.8 g of product are obtained (yield=52%).

m.p.=150° C., $[\alpha]_D^{20}$=–77.5 (c 1, ethanol).

Analysis

|       | C     | H    | N     |
|-------|-------|------|-------|
| Calc. | 45.37 | 5.92 | 11.76 |
| Found | 45.2  | 5.9  | 11.8  |

EXAMPLE 55

5-[[2-[[(4-L-thiazolidinyl)carbonyl]amino]-1-((2S)-2-methyl)-oxoethyl]amino]-5-deoxy-2-O-nitro-1,4:3,6-dianhydro-L-iditol monohydrochloride (62)

2 g of the above compound (61) are added to 14 ml of a 2N solution of hydrochloric acid in ethyl acetate. The solution is stirred for 5 hours at ambient temperature and the white solid formed is filtered off and then washed with ether. After recrystallisation from ethanol and then from methanol, 0.95 g of product is obtained (yield=54%).

m.p.: 185°–186° C. (dec), $[\alpha]_D^{20}$=–75.0 (c 1, water).

Analysis

|                           | C     | H    | N     | Cl   |
|---------------------------|-------|------|-------|------|
| Calc. (0.3 H$_2$O)        | 37.30 | 5.19 | 13.38 | 8.47 |
| Found                     | 37.3  | 5.1  | 13.3  | 8.6  |

EXAMPLE 56

5-[[2-[[(3-t-butoxycarbonyl-4-L-thiazolidinyl)carbonyl]amino]-1-((2S)-2-isopropyl)-oxoethyl]amino]-5-deoxy-2-O-nitro-1,4:3,6-dianhydro-L-iditol (63)

A solution of 2 g (6.9 mmols) of the base form corresponding to (10) in 70 ml of anhydrous dichloromethane is stirred at ambient temperature. 1.63 g (6.9 mmols) of N-t-Boc-L-thioproline, 1.43 g (6.9 mmols) of DCC and 0.95 g (6.9 mmols) of HOBt are added successively. After a reaction time of 20 hours and filtering off the DCU, 80 ml of dichloromethane are added and the washings are carried out as for (1). The oily residue obtained after evaporation is chromatographed on silica (230–400 mesh ASTM) and 2.55 g of a white paste are isolated and the latter is recrystallised from the ethyl acetate/diisopropyl ether mixture. 1.95 g of product are obtained (yield=56%).

m.p.=108°–109° C., $[\alpha]_D^{20}$=–57.5 (c 0.6, ethanol).

Analysis

|  | C | H | N |
|---|---|---|---|
| Calc. | 47.61 | 6.39 | 11.10 |
| Found | 47.5 | 6.4 | 11.2 |

EXAMPLE 57

5-[[2-[[(4-L-thiazolidinyl)carbonyl]amino]-1-((2S)-2-isopropyl)-oxoethyl]amino]-5-deoxy-2-O-nitro-1,4:3,6-dianhydro-L-iditol monohydrochloride (64)

5.9 g of the above compound (63) are added to 50 ml of a 2N solution of hydrochloric acid in ethyl acetate. The solution is stirred for 3 hours at ambient temperature and the white solid formed is filtered off then washed with ether. After recrystallisation from ethanol, 3 g of product are obtained (yield=58%).

m.p.=169° C. (dec), $[\alpha]_D^{20}$=–60.7 (c 1, water).

Analysis

|  | C | H | N | Cl |
|---|---|---|---|---|
| Calc. | 40.86 | 5.71 | 12.70 | 8.04 |
| Found | 40.9 | 5.6 | 12.6 | 8.0 |

EXAMPLE 58

5-[[2-[[(3-t-butoxycarbonyl-4-L-thiazolidinyl)carbonyl]amino]-1-((2S)-2-benzyl)-oxoethyl]amino]-5-deoxy-2-O-nitro-1,4:3,6-dianhydro-L-iditol (65)

A solution of 5 g (14.8 mmols) of the base form corresponding to (12) in 200 ml of anhydrous dichloromethane is stirred at ambient temperature. 3.45 g (14.8 mmols) N-t-Boc-n-thioproline, 3.05 g (14.8 mmols) of DCC and 2 g (14.8 mmols) of HOBt are added successively. After a reaction time of 20 hours, and filtering off the DCU, 100 ml of dichloromethane are added and washings are carried out as for (1). The pasty residue obtained after evaporation is chromatographed on silica (230–400 mesh ASTM) and 8.5 g of a white paste are isolated and the latter is recrystallised from ethyl acetate. 5.2 g of product are obtained (yield=63%).

m.p.=139°–140° C., $[\alpha]_D^{20}$=–68.7 (c 1, ethanol).

Analysis

|  | C | H | N |
|---|---|---|---|
| Calc. | 52.17 | 5.84 | 10.14 |
| Found | 52.3 | 5.9 | 10.1 |

EXAMPLE 59

5-[[2-[[(4-L-thiazolidinyl)carbonyl]amino]-1-((2S)-2-benzyl)-oxoethyl]amino]-5-deoxy-2-O-nitro-1,4:3,6-dianhydro-L-iditol monohydrochloride (66)

3.65 g of the above compound (65) are added to 23 ml of a 2N solution of hydrochloric acid in ethyl acetate. The solution is stirred for 15 hours at ambient temperature and the pasty solid formed is recovered and washed with ethyl acetate and then with ether. After recrystallisation from ethanol, 1.8 g of product are obtained (yield=55%).

m.p.=142°–152° C. (dec), $[\alpha]_D^{20}$=–25.0 (c 1, water).

Analysis

|  | C | H | N | Cl |
|---|---|---|---|---|
| Calc. (0.8 H$_2$O) | 45.33 | 5.32 | 11.13 | 7.04 |
| Found | 45.1 | 5.0 | 11.5 | 6.9 |

EXAMPLE 60

5-[[2-[[(3-t-butoxycarbonyl-4-L-thiazolidinyl)carbonyl]amino]-1-((2S)-2-(2'-thiomethyl)-ethyl)-oxoethyl]amino]-5-deoxy-2-O-nitro-1,4:3,6-dianhydro-L-iditol (67)

A solution of 7.2 g (22.4 mmols) of the base form corresponding to (38) in 220 ml of anhydrous dichloromethane is stirred at ambient temperature. 5.22 g (22.4 mmols) of N-t-Boc-L-thioproline, 4.62 g (22.4 mmols) of DCC and 3.03 g (22.4 mmols) of HOBt are added successively. After a reaction time of 20 hours, the DCU is filtered off and the solvent is evaporated. The oily residue is chromatographed on silica (230–400 mesh ASTM) and 11.9 g of a white solid are isolated and the latter is recrystallised from the ethyl acetate/diisopropyl ether mixture. 9.90 g of product are obtained (yield=82%).

m.p.=141° C., $[\alpha]_D^{20}$=–54.66 (c 0.6, ethanol).

Analysis

|  | C | H | N |
|---|---|---|---|
| Calc. | 44.76 | 6.01 | 10.44 |
| Found | 44.9 | 6.0 | 10.3 |

EXAMPLE 61

5-[[2-[[(4-n-thiazolidinyl)carbonyl]amino]-1-((2S)-2-(2'-thiomethyl)-ethyl)-oxoethyl]amino]-5-deoxy-2-O-nitro-1,4:3,6-dianhydro-L-iditol monohydrochloride (68)

8.5 g of the above compound (67) are added to 68 ml of a 1N solution of hydrochloric acid in ethyl acetate. The solution is stirred for 16 hours at ambient temperature and the white solid formed is filtered off and then washed with ethyl acetate and then with ether. After recrystallisation from methanol, 3.7 g of product are obtained (yield=49%).

m.p.=149° C., $[\alpha]_D^{20}$=−43.7 (c 1, water).

|  | C | H | N | Cl |
|---|---|---|---|---|
| Calc. | 38.09 | 5.32 | 11.84 | 7.49 |
| Found | 37.8 | 5.3 | 11.8 | 7.5 |

EXAMPLE 62

5-[[[(2S)-N-[(3-t-butoxycarbonyl-4-L-thiazolidinyl)carbonyl]-2-pyrrolidinyl]carbonyl]amino]-5-deoxy-2-O-nitro-1,4:3,6-dianhydro-L-iditol (69)

A solution of 5.11 g (17.7 mmols) of the base form corresponding to (14) in 200 ml of anhydrous dichloromethane is stirred at ambient temperature. 4.12 g (17.7 mmols) of N-t-Boc-L-thioproline, 3.65 g (17.7 mmols) of DCC and 2.39 g (17.7 mmols) of HOBt are added successively. After a reaction time of 24 hours and filtering off the DCU, 100 ml of dichloromethane are added and the washings are carried out as for (1). The yellow solid obtained after evaporation is chromatographed on silica (230–400 mesh ASTM) and 7.8 g of an oil which crystallises are isolated. After recrystallisation from the ethyl acetate, 5.4 g of product are obtained (yield=60%).

m.p.=161°–162° C., $[\alpha]_D^{20}$=−126.4 (c 1, ethanol).
Analysis

|  | C | H | N |
|---|---|---|---|
| Calc. | 47.80 | 6.02 | 11.15 |
| Found | 48.0 | 5.9 | 11.2 |

EXAMPLE 63

5-[[[(2S)-N-[(4-L-thiazolidinyl)carbonyl]-2-pyrrolidinyl]carbonyl]amino]-5-deoxy-2-O-nitro-1,4:3,6-dianhydro-L-iditol monohydrochloride (70)

2.86 g of the above compound (69) are added to 20 ml of a 2N solution of hydrochloric acid in ethyl acetate. The solution is stirred for 18 hours at ambient temperature and the white solid formed is filtered off and then washed with ether. After recrystallisation from methanol, 2.06 g of product are obtained (yield=82%).

m.p.=185° C. (dec), $[\alpha]_D^{20}$=−133 (c 1, water).
Analysis

|  | C | H | N | Cl |
|---|---|---|---|---|
| Calc. (0.1 H$_2$O + 0.05 HCl) | 40.70 | 5.29 | 12.65 | 8.40 |
| Found | 40.7 | 5.3 | 12.3 | 8.4 |

EXAMPLE 64

2-[[2-[[(4-L-thiazolidinyl)carbonyl]]amino]-1-oxoethyl]amino]-2-deoxy-5-O-nitro-1,4:3,6-dianhydro-D-glucitol monohydrochloride (71)

A suspension of 5.3 g (21.4 mmols) of the base form corresponding to (16) in 200 ml of anhydrous dichloromethane is stirred at ambient temperature. 5 g (21.4 mmols) of N-t-Boc-L-thioproline, 4.42 g (21.4 mmols) of DCC and 2.9 g (21.4 mmols) of HOBt are added successively. After a reaction time of 24 hours and filtering off the DCU, 100 ml of dichloromethane are added and the washings are carried out as for (1). The residue obtained after evaporation is chromatographed on silica (230–400 mesh ASTM) and 5.75 g (yield=58%) of a dry foam are isolated; it was not possible to crystallise the latter. The product is treated directly.

5.75 g of the above compound are added to 41 ml of a 2N solution of hydrochloric acid in ethyl acetate. The solution is stirred for 16 hours at ambient temperature and the white solid formed is filtered off and washed with ethyl acetate and then with ether. After recrystallisation from methanol, 2.6 g of product are obtained (yield=52%).

m.p.=195° C. (dec), $[\alpha]_D^{20}$=+24.5 (c 1, water).
Analysis

|  | C | H | N | Cl |
|---|---|---|---|---|
| Calc. | 36.13 | 4.80 | 14.04 | 8.89 |
| Found | 36.0 | 4.8 | 14.0 | 9.1 |

EXAMPLE 65

2-O-[2-[[(3-t-butoxycarbonyl-4-L-thiazolidinyl)carbonyl]amino]-1-oxoethyl]-5-O-nitro-1,4:3,6-dianhydro-D-glucitol (72)

A suspension of 2.07 g (7.27 mmols) of (2) in 60 ml of anhydrous dichloromethane is stirred at ambient temperature. 1.03 ml of triethylamine (7.33 mmols) are added, which gives rise to dissolution of the solid. 1.7 g (7.27 mmols) of N-t-Boc-L-thioproline, 3.08 g (7.27 mmols) of CMC and 0.98 g (7.27 mmols) of HOBt are added successively. After a reaction time of 24 hours, 140 ml of dichloromethane are added and the washings are carried out as for (1). The oil obtained after evaporation is chromatographed on silica (230–400 mesh ASTM) and 1.97 g of a solid are isolated and the latter is recrystallised from the ethyl acetate/petroleum ether mixture. 1.71 g of product are obtained (yield=50%).

m.p.=80°–82° C., $[\alpha]_D^{20}$=−11.1 (C 1, ethanol).
Analysis

|  | C | H | N |
|---|---|---|---|
| Calc. | 44.06 | 5.44 | 9.07 |
| Found | 44.1 | 5.3 | 9.0 |

EXAMPLE 66

2-O-[2-[[(4-L-thiazolidinyl)carbonyl]amino]-1-oxoethyl]-5-O-nitro-1,4:3,6-dianhydro-D-glucitol monohydrochloride (73)

A suspension of 3.7 g (13 mmols) of (2) in 100 ml of anhydrous dichloromethane is stirred at ambient temperature. 1.83 ml of triethylamine (13 mmols) are added, which gives rise to dissolution of the solid. 3.03 g (22.75 mmols) of L-thioproline, 2.68 g (13 mmols) of DCC and 1.76 g (13 mmols) of HOBt are added successively. After a reaction time of 24 hours, DCU is filtered off and the solvent is evaporated. The residue is chromatographed on silica (230–400 mesh ASTM) and 4.1 g of an oil are isolated. The latter is diluted in 80 ml of dichloromethane and hydrogen chloride is bubbled through the mixture for a few seconds. The hydrochloride precipitates in the form of a paste; after removal of the solvent and washing the paste with dichloromethane and then with ether, hardening of the product is observed; the latter forms a fine powder after filtering off. After triturations and washings with hexane and with ether, 2.84 g of product are finally obtained (yield=54%).

m.p.=103° C., $[\alpha]_D^{20}$=−24.2 (c 1, water).

Analysis

|  | C | H | N | Cl |
|---|---|---|---|---|
| Calc. (0.3 H$_2$O + 0.05 HCl) | 35.41 | 4.61 | 10.32 | 9.14 |
| Found | 35.4 | 4.6 | 10.1 | 9.0 |

EXAMPLE 67

5-O-[2-[[(4-L-thiazolidinyl)carbonyl]amino]-1-oxoethyl]-2-O-nitro-1,4:3,6-dianhydro-D-glucitol monohydrochloride (74)

A suspension of 6.04 g (21.21 mmols) of (3) in 200 ml of anhydrous dichloromethane is stirred at ambient temperature. 2.98 ml of triethylamine (21.21 mmols) are added, which gives rise to dissolution of the solid. 4.95 g (21.21 mmols) of N-t-Boc-L-thioproline, 8.99 g (21.21 mmols) of CMC and 2.87 g (21.21 mmols) of HOBt are added successively. After a reaction time of 24 hours, 100 ml of dichloromethane are added and the washings are carried out as for (1). The residue obtained after evaporation is chromatographed on silica (230–400 mesh ASTM) and 7.4 g of a dry foam are isolated; it was not possible to crystallise the latter. The product is treated directly.

7.2 g of the above compound are added to 62 ml of a 2N solution of hydrochloric acid in ethyl acetate. The solution is stirred for 18 hours at ambient temperature and after removal of the solvent, the residue is washed with acetate and then with ether. After crystallisation and recrystallisation from ethanol, 2.7 g of product are obtained (yield= 43%).

m.p.=85° C., $[\alpha]_D^{20}$=+8.3 (c 1, water).

Analysis

|  | C | H | N | Cl |
|---|---|---|---|---|
| Calc. (0.4 H$_2$O) | 35.41 | 4.65 | 10.32 | 8.71 |
| Found | 35.4 | 4.6 | 10.1 | 8.6 |

EXAMPLE 68

5-[[2-[[(3-acetyl-4-L-thiazolidinyl)carbonyl]amino]-1-oxoethyl]amino]-5-deoxy-2-O-nitro-1,4:3,6-dianhydro-L-iditol (75)

A solution of 3 g (12.13 mmols) of the base form corresponding to (6) in 120 ml of anhydrous dichloromethane is stirred at ambient temperature. 2.13 g (12.13 mmols) of N-acetyl-L-thioproline, 2.5 g (12.13 mmols) of DCC and 1.64 g (12.13 mmols) of HOBt are added successively. After a reaction time of 24 hours, and filtering off the DCU, 80 ml of dichloromethane are added and the washings are carried out as for (1). The oily residue, obtained after evaporation is chromatographed on silica (230–400 mesh ASTM). A solid is isolated which is recrystallised successively from ethyl acetate and then from methanol. 2.2 g of product are obtained (yield=44%).

m.p.=147°–148° C., $[\alpha]_D^{20}$=−66.4 (c 1, water).

Analysis

|  | C | H | N |
|---|---|---|---|
| Calc. | 41.58 | 4.99 | 13.85 |
| Found | 41.3 | 4.8 | 13.8 |

EXAMPLE 69

5-[[2-[[(3-benzoyl-4-L-thiazolidinyl)carbonyl]amino]-1-oxoethyl]amino]-5-deoxy-2-O-nitro-1,4:3,6-dianhydro-L-iditol (76)

A solution of 1 g (4.05 mmols) of the base form corresponding to (6) in 60 ml of anhydrous dichloromethane is stirred at ambient temperature. 1.24 g (5.25 mmols) of N-benzoyl-L-thioproline, 1.08 g (5.25 mmols) of DCC and 0.71 g (5.25 mmols) of HOBt are added successively. After a reaction time of 24 hours, and filtering off the DCU, 40 ml of dichloromethane are added and the washings are carried out as for (1). The residue obtained after evaporation is chromatographed on silica (230–400 mesh ASTM). A white solid is isolated which is recrystallised from ethanol. 0.65 g of product is obtained (yield=26%).

m.p.=135°–136° C.

Analysis

|  | C | H | N |
|---|---|---|---|
| Calc. (0.2 H$_2$O) | 48.54 | 4.79 | 11.91 |
| Found | 48.5 | 4.7 | 11.8 |

EXAMPLE 70

5-[[[[2-[(Phenylmethyl)thio]benzoyl]amino]-1-oxoethyl]amino]-5-deoxy-2-O-nitro-1,4:3,6-dianhydro-L-iditol (47)

A solution of 2 g (8.09 mmol) of the base form corresponding to (6) in 70 ml of anhydrous dichloromethane is stirred at ambient temperature. 2 g (8.19 mmol) of S-benzylthiosalicylic acid and 1.68 g (8.19 mmol) of DCC are added successively. After reaction for 24 hours, filtering off DCU and evaporation of the solvent, the oil obtained is chromatographed (silica, 230–400 mesh ASTM); the compound isolated is recrystallised from methanol. 2.08 g are obtained (Yield=54%).

m.p.=113° C., $[\alpha]_D^{20}$ecryst2.5 (c 0.4 ethanol).

Analysis

|  | C | H | N |
|---|---|---|---|
| Calc. | 55.80 | 4.89 | 8.87 |
| Found | 55.6 | 4.9 | 8.8 |

III-b: R—CO—A+Y—B:

Table IV below shows the derivatives synthesised by this method.

TABLE IV

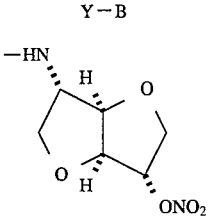

48

EXAMPLE 71

5-[[2-[[(3-Formyl-2,2-dimethyl-4-L-thiazolidinyl)carbonyl]amino]-1-oxoethyl]amino]-5-deoxy-2-O-nitro-1,4:3,6-dianhydro-L-iditol (48)

A solution of 2.85 g (15 mmol) of 5-amino-1,4:3,6-dianhydro-5-deoxy-L-iditol 2-nitrate in 90 ml of anhydrous dichloromethane is stirred at ambient temperature. 3.07 g (12.4 mmol) of N-[4-(3-formyl-2,2-dimethyl-L-thiazolidine)carbonyl]-glycine, 2.58 g (12.5 mmol) of DCC and 1.68 g (12.4 mmol) of HOBt are added successively. After a reaction time of 22 hours, DCU is filtered off and the solvent is evaporated; the oily residue is chromatographed on silica (230–400 mesh ASTM) and the compound is isolated, which compound is recrystallised from methanol and then from ethanol. 2.82 g are obtained (Yield=54%).

m.p.=142°–143° C., $[\alpha]_D^{20}$=+29.3 (c 2, acetone).

Analysis

|  | C | H | N |
|---|---|---|---|
| Calc. | 43.05 | 5.30 | 13.39 |
| Found | 43.2 | 5.2 | 13.4 |

IV—SYNTHESIS OF THE COMPOUNDS OF FORMULA I WHERE n=0 AND R$_2$=CO—X

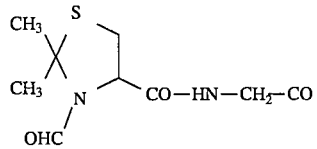

77

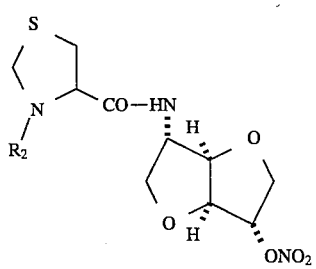

-continued

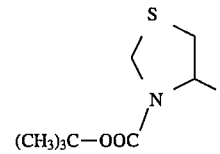

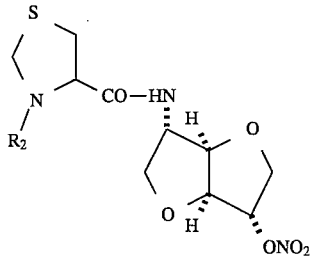

78

EXAMPLE 72

5-[[[(4R)-N-[(3-t-butoxycarbonyl-4-L-thiazolidinyl)carbonyl]-4-thiazolidinyl]carbonyl]amino]-5-deoxy-2-O-nitro-1,4:3,6-dianhydro-L-iditol (77)

A solution of 4.65 g (15.2 mmols) of the base form corresponding to (30) in 250 ml of anhydrous dichloromethane is stirred at ambient temperature. 3.55 g (15.2 mmols) of N-t-Boc-L-thioproline, 3.14 g (15.2 mmols) of DCC and 2.06 g (15.2 mmols) of HOBt are added successively. After a reaction time of 48 hours, the DCU is filtered off and the solvent is evaporated. The oily residue is chromatographed on silica (230–400 mesh ASTM) and a white solid is isolated which is recrystallised from a methanol/diisopropyl ether mixture and then from methanol. 3.2 g of product are obtained (yield=40%).

m.p.=156° C., $[\alpha]_D^{20}$=−159.1 (c 1, ethanol).

Analysis

|  | C | H | N |
|---|---|---|---|
| Calc. | 43.84 | 5.42 | 10.76 |
| Found | 43.6 | 5.3 | 10.8 |

EXAMPLE 73

5-[[[(4R)-N-[(4-L-thiazolidinyl)carbonyl]-4-thiazolidinyl]carbonyl]amino]-5-deoxy-2-O-nitro-1,4:3,6-dianhydro-L-iditol monohydrochloride (78)

1.8 g of the above compound (77) are added to 12 ml of a 2N solution of hydrochloric acid in ethyl acetate. The solution is stirred for 18 hours at ambient temperature and the white solid formed is filtered off and washed with ethyl acetate and then with ether. After recrystallisation from methanol, 0.83 g of product is obtained (yield=52%).

m.p.=174° C. (dec), $[\alpha]_D^{20}$=−174.9 (C 1, water).

Analysis

|       | C     | H    | N     | Cl   |
|-------|-------|------|-------|------|
| Calc. | 36.80 | 4.63 | 12.26 | 7.76 |
| Found | 36.8  | 4.6  | 12.3  | 7.8  |

PHARMACOLOGICAL REPORT RELATING TO THE COMPOUNDS ACCORDING TO THE INVENTION

PHARMACOLOGICAL TESTS;

EXAMPLE A

Vasorelaxant effect of the compounds according to the invention on isolated vessels.

Adult Wistar rats weighing between 250 and 350 g are anaesthetised by intraperitoneal injection of sodium pentobarbital (30 mg/kg). The thoracic aorta is rapidly removed and placed in a refrigerated and oxygenated solution of bicarbonate buffer of the Krebs-Ringer type (composition [mM]: NaCl, 118 ; KCl, 4.7 ; $CaCl_2$, 2.5 ; $MgSO_4$, 1.2 ; $KH_2PO_4$, 1.2 ; $NaHCO_3$, 25.0; disodium calcium salt of EDTA, 0.026; glucose 11.1). The aorta is dissected with the aim of removing the connective tissue and then cut into 6 rings (length 5–10 mm). The endothelium is removed by moderate abrasion of the intimal surface of the aortic segments with the aid of a pair of tweezers. These segments are then placed between two hooks in an isolated organ cell filled with 25 ml of bicarbonate buffer (pH 7.4), thermostat-controlled at 37° C. and oxygenated with the aid of a 95% $O_2$/5% $CO_2$ mixture (pH 7.4). One of the hooks is fixed to a fixed point, while the second is connected to a transducer with the aim of measuring the variations in isometric voltage (expressed in grams). After an equilibration period of 30 min., the segments are progressively withdrawn so as to attain the level of base voltage for which the contractor response to noradrenalin ($10^{-7}$M) is maximum (optimum voltage; average 2 g). The absence of endothelium is verified by addition of a single concentration of acetylcholine ($10^{-6}$M), after precontraction of the vessels by noradrenalin ($10^{-7}$M). The integrity of the vascular smooth muscle is also verified by adding a single concentration of a vasodilator whose response is independent of the presence of the endothelium, SIN-1 ($10^{-5}$M). After this initial procedure, the aortas are washed, equilibrated for a period of 30 min and then recontracted ($10^{-7}$M noradrenalin). The relaxant effect of the substance to be tested is then evaluated by adding increasing concentrations of this substance (from $10^{-8}$ to $10^{-4}$M). The maximum inhibition of the concentration caused by noradrenalin (expressed as a percentage) is then calculated ("maximum relaxation"). When this maximum relaxation is greater than 50%, the concentration of substance tested producing a 50% inhibition of the maximum contraction ($IC_{50}$) is calculated. Table V below collates the $IC_{50}$ and the maximum relaxation percentages for the various compounds tested.

TABLE V

| Number | $IC_{50}$ (µM) | Maximum Relaxation |
|--------|----------------|--------------------|
| 22     | 10             | 100%               |
| 30     | 10             | 100%               |
| 48     | >100           | 25%                |
| 28     | 50             | 70%                |
| 39     | 50             | 80%                |
| 6      | >100           | 45%                |
| 4      | 20             | 75%                |
| 5      | 25             | 70%                |
| 46     | 100            | 50%                |
| 32     | 15             | 100%               |
| 33     | >100           | 50%                |
| 34     | >100           | 25%                |
| 20     | 28             | 85%                |
| 31     | 25             | 83%                |
| 40     | >100           | 38%                |
| 41     | 63             | 70%                |
| 42     | 33             | 92%                |
| 15     | 60             | 58%                |
| 16     | >100           | 41%                |
| 1      | 32             | 83%                |
| 8      | 32             | 80%                |
| 37     | 13             | 100%               |
| 2      | 100            | 52%                |
| 14     | 14             | 98%                |
| 7      | 17             | 96%                |
| 13     | 49             | 74%                |
| 3      | 79             | 63%                |
| 11     | 25             | 100%               |
| 35     | 100            | 46%                |
| 26     | 80             | 70%                |
| 27     | >100           | 14%                |
| 9      | 80             | 70%                |
| 18     | 72             | 75%                |
| 19     | >100           | 40%                |
| 24     | 20             | 100%               |
| 25     | >100           | 35%                |
| 43     | 32             | 80%                |
| 12     | 2,5            | 100%               |
| 21     | 100            | 31%                |
| 63     | 70             | 70%                |
| 60     | 87             | 53%                |
| 67     | 9              | 100%               |
| 49     | 38             | 100%               |
| 61     | 32             | 100%               |
| 77     | 40             | 97%                |
| 69     | 42             | 87%                |
| 65     | 20             | 100%               |
| 62     | 55             | 72%                |
| 64     | 51             | 84%                |
| 70     | 35             | 83%                |
| 68     | 29             | 90%                |
| 72     | 64             | 67%                |
| 73     | 53             | 66%                |
| 71     | 70             | 66%                |
| 78     | 20             | 89%                |

In general, the products which have a maximum relaxation greater than 80% with an $IC_{50}$ of less than 50 µM are regarded as particularly valuable; however, this Table does not take into account the data relating to the tachyphylaxis, and some products, such as (46), may be of value if this additional criterion is taken into account.

EXAMPLE B

Haemodynamic effects of the compounds according to the invention in unanaesthetised hypertensive dogs (n=3).

Table VI below and FIG. 1 show more particularly the change in the effect of compound (46) on the various haemodynamic parameters as a function of time, the compound being administered p.o. in a dosage of 3 mg/kg. Compound (46) lowers the systolic blood pressure (BPs) and the left ventricular end-diastolic pressure (LVEDP) in a significant, pronounced and prolonged manner. FIGS. 1 (FIGS. 1a, 1b, 1c, 1d and 1e) illustrate these results and show the variations (Δ) in the following haemodynamic parameters: BPs (FIG. 1a), BPd (FIG. 1b), LVEDP (FIG. 1c), HR (FIG. 1d) and vasorelaxant activity (FIG. 1e).

TABLE VI

A. Parameters:

|  | bv | 0 | 10 | 20 | 30 | 60 | 90 | 120 | 180 | 240 | 300 | 360 |
|---|---|---|---|---|---|---|---|---|---|---|---|---|
| BPs | 150 | 0 | −5 | 0 | 0 | −25 | −30 | −30 | −15 | −15 | −15 | −10 |
|  | 185 | 0 | 0 | 0 | 0 | −15 | −25 | −25 | −25 | −35 | −45 | −25 |
|  | 155 | 0 | −10 | −5 | −5 | −25 | −30 | −30 | −35 | −40 | −40 | −35 |
|  | 75 | 0 | −5 | 0 | 5 | 5 | 5 | 5 | 10 | 10 | 10 | 10 |
| BPd | 85 | 0 | 0 | 0 | 0 | 0 | 10 | 10 | 15 | 15 | 15 | 15 |
|  | 70 | 0 | −5 | 0 | 0 | −5 | −5 | 0 | 0 | 0 | 0 | 0 |
|  | 17 | 0 | −1 | −3 | 0 | −7 | −7 | −9 | −7 | −7 | −4 | −5 |
| LVEDP | 13 | 0 | 0 | 0 | 0 | −3 | −6 | −7 | −4 | −5 | 0 | −3 |
|  | 9 | 0 | −2 | −2 | −3 | −3 | −3 | −2 | −4 | −4 | −3 | −4 |
|  | 2500 | 0 | −100 | 300 | 0 | 0 | −200 | −400 | −300 | −500 | −300 | −500 |
| dp/dt | 2300 | 0 | 0 | 0 | 500 | 500 | 500 | 800 | 500 | 500 | 800 | 500 |
|  | 2400 | 0 | −400 | −200 | −200 | −400 | −400 | −400 | −200 | −400 | −400 | −400 |
|  | 80 | 0 | 0 | 35 | 0 | 10 | 35 | 55 | 35 | 40 | 45 | 15 |
| HR | 95 | 0 | 10 | 0 | 10 | −10 | 45 | 63 | 40 | 20 | 40 | 10 |
|  | 115 | 0 | 0 | 15 | 10 | −20 | −10 | −20 | 20 | 20 | −5 | 15 |

B. Averages: (n = 3)

|  | vb | 0 | 10 | 20 | 30 | 60 | 90 | 120 | 180 | 240 | 300 | 360 |
|---|---|---|---|---|---|---|---|---|---|---|---|---|
| BPs average | 163 | 0 | −5 | −2 | −2 | −22 | −28 | −28 | −25 | −30 | −27 | −23 |
| SEM | 11 | 0 | 3 | 2 | 2 | 3 | 2 | 2 | 6 | 8 | 7 | 7 |
| BPd average | 77 | 0 | −3 | 0 | 2 | 0 | 3 | 5 | 8 | 8 | 8 | 8 |
| SEM | 4 | 0 | 2 | 0 | 2 | 3 | 4 | 3 | 4 | 4 | 4 | 4 |
| LVEDP average | 13 | 0 | −1 | −2 | −1 | −4 | −5 | −6 | −5 | −5 | −2 | −4 |
| SEM | 2 | 0 | 1 | 1 | 1 | 1 | 1 | 2 | 1 | 1 | 1 | 1 |
| dp/dt average | 2400 | 0 | −167 | 33 | 100 | 33 | −33 | 0 | 0 | −133 | 33 | −133 |
| SEM | 58 | 0 | 120 | 145 | 208 | 260 | 273 | 400 | 252 | 318 | 384 | 318 |
| HR average | 97 | 0 | 3 | 17 | 7 | −7 | 23 | 33 | 32 | 27 | 27 | 13 |
| SEM | 10 | 0 | 3 | 10 | 3 | 9 | 17 | 27 | 6 | 7 | 16 | 2 |

BPs = cystolic blood pressure
BPd = diastolic blood pressure
LVEDP = left ventricular end-diastolic pressure
dp/dt = vasorelaxant activity
HR = heart rate
bv = base value

EXAMPLE C

Haemodynamic effects of the compounds according to the invention on anesthetised pigs or dogs Pigs are of "German land" race (20–26 kg) and are used after fasting overnight.

The dogs, weighing between 16 and 26 kg, are the progeny of a labrador/harrier cross.

In the case of pigs, sedation, analgesia and anesthesia are induced by ketamine HCl (20 mg/kg i.m.), methonidate HCl (10 mg/kg i.m.), xylacine HCl (3 mg/kg i.m.) and sodium pentobarbitol (25–30 mg/kg as bolus i.v. or 0.16 mg/kg/min as i.v. perfusion).

In the case of dogs the anesthesia is induced by sodium pentobarbitol (45 mg/jg i.v.) and maintained with an i.v. perfusion (flow rate of 8 mg/kg/h).

The pigs or dogs are placed under artificial respiration in ambient air. Analysis of the blood gases ($pO_2$, $pCO_2$) is carried out at regular intervals and oxygen can be supplied via the respirator, if necessary.

The haemodynamic parameters recorded include the left ventricular pressure (LVP; Millar PC350 Tip catheter inserted via the carotid artery), systemic blood pressure (BPs, BPd; full catheter in a femoral artery), the end pressure of the left ventricular diastole (LVEDP), the ventricular contractility ($LVPdp/dt_{max}$) and the heart rate (HR).

Following an equilibration period of the order of 45 minutes, the compounds studied are administered intraduodenally (i.d.) or intraveinously (i.v.) to several animals (1 to 4). The haemodynamic variables are recorded continuously for 1 to 3 hours, as a function of the period of action of the compound.

The effects of the compounds studied are shown as the absolute difference with respect to the base value (bv) measured before administration of the compounds and are shown in Table VII (a,b,c).

An antianginal activity is estimated by a fall in the BPs and the LVEDP (fall in venous return).

TABLE VIIa (i.d.)
Haemodynamic effects in pigs.

| Compound | Dosage (mg/kg i.d.) | BPs (mmHg) | (min) | LVRDP (mmHg) | (min) |
|---|---|---|---|---|---|
| 6 | 1,0 | −31 | >180 | −4,0 | >180 |
| 5 | 1,0 | −24 | >120 | −4,0 | >120 |
| 30 | 3,0 | −40 | >60 | −2,0 | >60 |
| 28 | 3,0 | −28 | >180 | −6,0 | >180 |

TABLE VIIa-continued (i.d.)
Haemodynamic effects in pigs.

| Compound | Dosage (mg/kg i.d.) | BPs (mmHg) | (min) | LVRDP (mmHg) | (min) |
|---|---|---|---|---|---|
| 4 | 3,0 | −28 | >120 | −2,0 | >120 |
| 46 | 3,0 | −30 | >120 | −5,0 | >120 |
| 32 | 3,0 | −30 | >180 | −4,0 | >180 |
| 48 | 10,0 | −25 | >180 | −4,0 | >180 |
| 39 | 10,0 | −5 | >90 | −1,0 | >90 |
| 47 | 10,0 | −10 | >120 | −1,0 | >90 |
| 33 | 10,0 | −12 | >60 | −3,0 | >60 |
| 34 | 10,0 | −22 | >180 | −4,0 | >180 |
| 23 | 10,0 | 0 | | 0 | |
| 31 | 10,0 | −15 | >60 | −2,0 | >60 |
| IS-5-MN | 1,0 | 0 | | 0 | |
| IS-5-MN | 3,0 | −5 | 60 | −3 | 60 |
| IS-5-MN | 10,0 | −26 | >120 | −3,0 | >120 |

TABLE VIIb (i.v.)
Haemodynamic effects in pigs.

| Compound | Dosage (mg/kg i.d.) | BPs (mmHg) | (min) | LVRDP (mmHg) | (min) |
|---|---|---|---|---|---|
| 29 | 3 | −42 | 10 | −2,0 | 16 |
| ? | 3 | −10 | 5 | 0,0 | 0 |
| 22 | 10 | −73 | 5 | −2,0 | 5 |
| 20 | 10 | −20 | 5 | −4,0 | 5 |

TABLE VIIc (i.d.)
Haemodynamic effects in dogs.

| Compound | Dosage (mg/kg i.d.) | BPs (mmHg) | (min) | LVEDP (mmHg) | (min) |
|---|---|---|---|---|---|
| 68 | 1 | −30 | >180 | −3,0 | >180 |
| 49 | 1,1 | −32 | >240 | | |
| 41 | 3 | −25 | >180 | 0,0 | 0 |
| 15 | 3 | −20 | >180 | −3,0 | >180 |
| 8 | 3 | −30 | >150 | | |
| 13 | 3 | −30 | >120 | | |
| 3 | 3 | −10 | >60 | −4,5 | >60 |
| 12 | 3 | −30 | >240 | | |
| 21 | 3 | −5 | >60 | −2,0 | >60 |
| 9 | 3 | 5 | >60 | 0,0 | 0 |
| 60 | 3 | −15 | >60 | 0,0 | 0 |
| 67 | 3 | −15 | >90 | −1,5 | >90 |
| 61 | 3 | −25 | >180 | −1,5 | >180 |
| 77 | 3 | −35 | >180 | −2,0 | >180 |
| 69 | 3 | −40 | >150 | −2,5 | >150 |
| 65 | 3 | 0 | 0 | 1,0 | 30 |
| 62 | 3 | −35 | >30 | | |
| 64 | 3 | −25 | >180 | −2,0 | 150 |
| 70 | 3 | −30 | >90 | 0,0 | 0 |
| 71 | 3 | 0 | 0 | −5,5 | >60 |
| 78 | 3 | −13 | 150 | −1,0 | 90 |
| 25 | 10 | −30 | >60 | −3,0 | >60 |

TABLE VIId (i.v.)
Haemodynamic effects in dogs.

| Compound | Dosage (mg/kg i.v.) | BPs (mmHg) | (min) | LVEDP (mmHg) | (min) |
|---|---|---|---|---|---|
| 45 | 3 | −10 | >120 | 0,0 | 0 |
| 40 | 3 | −10 | >90 | −1,0 | >90 |
| 1 | 3 | 5 | 10 | 1,0 | 10 |
| 2 | 3 | −10 | >120 | −1,0 | >120 |
| 14 | 3 | −10 | >90 | −2,0 | >90 |
| 7 | 3 | −20 | >90 | −2,0 | >90 |
| 11 | 3 | −10 | >30 | 0,0 | 0 |
| 35 | 3 | −10 | >30 | 0,0 | 0 |
| 27 | 3 | −15 | >90 | −1,0 | >90 |
| 63 | 3 | −20 | >60 | −1,0 | 60 |
| 24 | 3 | −10 | >30 | 1,0 | 10 |
| 73 | 3 | −15 | 60 | −2,0 | 60 |
| 42 | 10 | −10 | >90 | 0,0 | 0 |
| 16 | 10 | −5 | >30 | −1,0 | >30 |
| 37 | 10 | −25 | >90 | −2,0 | 30 |
| 26 | 10 | −10 | >90 | 2,0 | >90 |
| 18 | 10 | −10 | >30 | 3,0 | >30 |
| 19 | 10 | −35 | >60 | 0,0 | 0 |
| 43 | 10 | −20 | 90 | −1,0 | 60 |
| 72 | 10 | 0 | 0 | 0,0 | 0 |

EXAMPLE D

Determination of the relaxant activity of the compounds according to the invention on blood vessels isolated from guinea pigs.

The pulmonary artery of male guinea pigs (350–500 g) is isolated and cut into spiral tracts (1 mm wide, 15 mm long). The latter are arranged in an organ cell at 30° C. filled with a 0.9% NaCl solution and oxygenated with the aid of a 95% $O_2$/5% $CO_2$ mixture (Tyrode, pH 7.4), in order to measure the variations in length. After having removed the calcium from the tissues (Tyrode without calcium and 0.2 mM EDTA), the tracts are depolarised in the presence of a concentrated solution of $K^+$ ions (40 mM), which is produced by replacing the NaCl by equimolar amounts of KCl, and a contraction of long duration is then induced by $Ca^{2+}$ ions (0.5 mM).

The compounds studied are then introduced into the organ cell in increasing concentrations.

Each compound is tested on at least four vessel spiral tracts.

The relaxation power of the compounds is determined by calculating the concentrations which give a relaxation of 50% ($IC_{50}$), from concentration/effect curves. Table VIII illustrates these results.

TABLE VIII

Relaxant effects on the isolated pulmonary vessel in guinea pigs.

| Compound | $IC_{50}$ (µM) |
|---|---|
| 6 | 30 |
| 5 | 14 |
| 30 | 32 |
| 28 | 2 |
| 4 | 6 |
| 46 | 38 |
| 48 | >100 |
| 39 | 1 |
| 47 | 2 |
| 22 | 3 |

TABLE VIII-continued

| Relaxant effects on the isolated pulmonary vessel in guinea pigs. | |
|---|---|
| Compound | IC$_{50}$ (µM) |
| IS-5-MN | >100 |

The IC$_{50}$ illustrates the relaxant effect on the isolated pulmonary vessel.

EXAMPLE E

Absence of tachyphylaxis in dogs. Comparison with isosorbide mononitrate (IS-5-MN).

The product (46) is tested in a tachyphylaxis model on anaesthetised dogs. IS-5-MN is used as reference substance.

8 dogs of each sex, weighing between 16 and 24 kg, are used. These dogs are the progeny of a labrador/harrier cross. Anaesthesia is induced with the aid of sodium pentobarbital (45 mg/kg i.v.) and maintained by i.v. perfusion (flow rate: 8 mg/kg/h). The animals are ventilated, with the aid of a "Bird Mark 7" respirator, using ambient air, and catheterised. The systemic peripheral blood pressure (BPs) is measured in the femoral artery using a pressure transducer (Combitrans, B. Braun Melsungen AG, 3508 Delsungen, Germany). The arterial blood gases are measured at regular intervals.

Compound (46) is administered intraduodenally (i.d.) in a dosage of 0.75 mg/kg and using a volume of 10 ml/animal, dissolved in water. IS-5-MN is also dissolved in water and given i.d. in a dosage of 5 mg/kg in a volume of 10 ml/animal.

Three hours (in the case of IS-5-MN) or four hours (in the case of (46)) after the first administration, the compounds are readministered in the same dosage and by the same route. The haemodynamic parameter chosen for the study of the tachyphylaxis is the systolic blood pressure (BPs), insofar as this parameter is very sensitive to the administration of the compounds.

At the time of the second administration of the compounds according to the invention, the BPs has approximately returned to the control value (before the first administration).

The results obtained are given in Tables IX and X, which correspond to FIGS. 2 [2a (control: IS-5-MN) and 2b (compound (46))] which illustrate the effect, as a function of time, of a repeated administration of these products on the BPs in anaesthetised dogs; the curves (-o-) correspond to the first administration and the curves (...o...) correspond to the second administration.

TABLE IX.A

First administration of IS-5-MN

1. Parameters:

| | bv | 0 | 5 | 10 | 15 | 30 | 60 | 120 | 180 |
|---|---|---|---|---|---|---|---|---|---|
| BPs | 140 | 0 | −25 | −25 | −25 | −35 | −35 | 0 | −5 |
| | 135 | 0 | −35 | −25 | −20 | −20 | −10 | 0 | 0 |
| | 160 | 0 | −30 | −30 | −30 | −25 | −25 | −15 | −15 |
| | 135 | 0 | −30 | −25 | −25 | −15 | −20 | −5 | 5 |
| BPd | 90 | 0 | −15 | −15 | −15 | −15 | −20 | 10 | 5 |
| | 90 | 0 | −25 | −15 | −10 | −10 | 0 | 0 | 0 |
| | 110 | 0 | −20 | −20 | −20 | −15 | −15 | −5 | −5 |
| | 90 | 0 | −25 | −20 | −20 | −10 | −15 | 5 | 10 |
| LVEDP | 15 | 0 | −3 | −3 | −3 | −1 | 0 | −1 | −3 |
| | 10 | 0 | −4 | −5 | −5 | −5 | −2 | −1 | −1 |
| | 13 | 0 | −3 | −3 | −3 | −3 | −3 | −3 | −5 |
| | 12 | 0 | −2 | −1 | −1 | −1 | −1 | −2 | 0 |
| dp/dt | 1400 | 0 | −200 | −300 | −200 | −300 | −400 | 400 | 100 |
| | 1600 | 0 | −100 | 0 | 0 | 0 | 0 | 0 | 100 |
| | 2000 | 0 | −100 | −100 | −100 | −100 | −100 | 0 | 100 |
| | 2100 | 0 | −300 | −300 | −300 | −300 | −300 | −100 | 100 |
| HR | 140 | 0 | 0 | 0 | −5 | −15 | −20 | 0 | −5 |
| | 125 | 0 | 0 | 5 | 5 | 5 | 10 | 10 | 10 |
| | 130 | 0 | 5 | 5 | 5 | 0 | −5 | 0 | 5 |
| | 140 | 0 | 0 | 0 | 0 | 0 | 0 | 5 | 10 |

2. Averages:

| | bv | 0 | 5 | 10 | 15 | 30 | 60 | 120 | 180 |
|---|---|---|---|---|---|---|---|---|---|
| BPs | 143 | 0 | −30 | −26 | −25 | −24 | −23 | −5 | −4 |
| average SEM | 6 | 0 | 2 | 1 | 2 | 4 | 5 | 4 | 4 |
| BPd | 95 | 0 | −21 | −18 | −16 | −13 | −12 | 3 | 3 |
| average, SEM | 5 | 0 | 2 | 1 | 2 | 1 | 4 | 3 | 3 |
| LVEDP | 13 | 0 | −3 | −3 | −3 | −3 | −1 | −2 | −2 |
| average SEM | 1 | 0 | 0 | 1 | 1 | 1 | 1 | 0 | 1 |
| dp/dt | 1775 | 0 | −175 | −175 | −150 | −175 | −200 | 75 | 100 |
| average | 165 | 0 | 48 | 75 | 65 | 75 | 91 | 111 | 0 |

TABLE IX.A-continued

First administration of IS-5-MN

| | | | | | | | | |
|---|---|---|---|---|---|---|---|---|
| SEM | | | | | | | | |
| HR | 134 | 0 | 1 | 3 | 1 | −2 | −4 | 4 | 5 |
| average | 4 | 0 | 1 | 1 | 2 | 4 | 6 | 2 | 4 |
| SEM | | | | | | | | |

TABLE IX.B

Second administration of IS-5-MN

1. Parameters:

| | | | | TIME (min) | | | | |
|---|---|---|---|---|---|---|---|---|
| | bv | 0 | 5 | 10 | 15 | 30 | 60 | 120 | 180 |
| BPs | 135 | 0 | −15 | −15 | −15 | −10 | 0 | −5 | −5 |
| | 135 | 0 | −20 | −15 | −15 | −10 | −10 | −15 | −5 |
| | 145 | 0 | −20 | −15 | −10 | −5 | −15 | −5 | 0 |
| | 140 | 0 | −20 | −15 | −10 | −10 | −5 | 0 | −5 |
| BPd | 90 | 0 | −5 | −5 | −5 | 0 | 5 | 0 | 0 |
| | 95 | 0 | −15 | −15 | −15 | −10 | −10 | −15 | −5 |
| | 105 | 0 | −15 | −15 | −10 | −5 | −10 | −5 | 0 |
| | 100 | 0 | −15 | −10 | −5 | −5 | 0 | 0 | 0 |
| LVEDP | 12 | 0 | −2 | −2 | −2 | −2 | −2 | −2 | −2 |
| | 9 | 0 | −2 | −2 | −1 | −1 | −3 | −2 | −3 |
| | 8 | 0 | 0 | −1 | 0 | 0 | −1 | 1 | −1 |
| | 12 | 0 | −2 | −2 | −2 | −2 | −1 | −2 | −2 |
| dp/dt | 1400 | 0 | −200 | −200 | −100 | 0 | 100 | 0 | 100 |
| | 1700 | 0 | −100 | 0 | −100 | 0 | 0 | 0 | 200 |
| | 2100 | 0 | −100 | −100 | −100 | 0 | −100 | 100 | 300 |
| | 2200 | 0 | −100 | 0 | −100 | 0 | 200 | 300 | 100 |
| HR | 135 | 0 | 0 | 0 | −5 | 0 | 5 | 5 | 5 |
| | 135 | 0 | 0 | 5 | 0 | 5 | 0 | 5 | 15 |
| | 135 | 0 | 0 | 5 | 5 | 0 | −5 | −5 | 0 |
| | 150 | 0 | 5 | 5 | 0 | 0 | 0 | 10 | 5 |

2. Averages: (n = 4)

| | | | | TIME (min) | | | | |
|---|---|---|---|---|---|---|---|---|
| | bv | 0 | 5 | 10 | 15 | 30 | 60 | 120 | 180 |
| BPs | 139 | 0 | −19 | −15 | −13 | −9 | −7 | −6 | −4 |
| average SEM | 2 | 0 | 1 | 0 | 1 | 1 | 3 | 3 | 1 |
| BPd | 98 | 0 | −13 | −11 | −9 | −5 | −4 | −5 | −1 |
| average SEM | 3 | 0 | 3 | 2 | 2 | 2 | 4 | 4 | 1 |
| LVEDP | 10 | 0 | −1 | −2 | −1 | −1 | −2 | −1 | −2 |
| average sem | 1 | 0 | 1 | 0 | 1 | 1 | 0 | 1 | 0 |
| dp/dt | 1850 | 0 | −125 | −75 | −100 | 0 | 50 | 100 | 175 |
| average SEM | 185 | 0 | 25 | 48 | 0 | 0 | 65 | 71 | 48 |
| HR | 139 | 0 | 1 | 4 | 0 | 1 | 0 | 4 | 6 |
| average SEM | 4 | 0 | 1 | 1 | 2 | 1 | 2 | 3 | 3 |

TABLE X.A

First administration of compound (46)

1. Parameters:

| | | | | TIME (min) | | | | |
|---|---|---|---|---|---|---|---|---|
| | bv | 5 | 10 | 15 | 30 | 60 | 120 | 180 | 240 |
| BPs | 130 | −5 | −15 | −25 | −30 | −30 | −30 | −25 | −15 |
| | 145 | −5 | −20 | −25 | −30 | −35 | −35 | −30 | −20 |
| | 120 | −10 | −20 | −20 | −20 | −15 | −15 | −10 | 0 |
| | 145 | 0 | −15 | −35 | −40 | −50 | −45 | −30 | −15 |
| BPd | 80 | −5 | −10 | −15 | −20 | −20 | −20 | −20 | −10 |
| | 95 | −5 | −10 | −15 | −20 | −25 | −25 | −20 | −20 |

TABLE X.A-continued

First administration of compound (46)

|  | | | | | | | | |
|---|---|---|---|---|---|---|---|---|
|  | 80 | −5 | −10 | −15 | −15 | −10 | −10 | −5 | 0 |
|  | 90 | 0 | −15 | −20 | −25 | −25 | −25 | −15 | 0 |
| LVEDP | 9 | 0 | −2 | −3 | −4 | −3 | −2 | −3 | −4 |
|  | 10 | −1 | −2 | −2 | −2 | −3 | −2 | −2 | −3 |
|  | 10 | 0 | 0 | 1 | 1 | −2 | −6 | −7 | −7 |
|  | 13 | 0 | −3 | −3 | −4 | −4 | −4 | −4 | −3 |
| dp/dt | 1100 | 0 | −100 | −100 | −100 | −200 | −200 | −200 | −100 |
|  | 1300 | 0 | −100 | −100 | −200 | −300 | −300 | −300 | −100 |
|  | 1200 | 0 | −100 | −100 | −100 | 0 | −200 | −100 | 0 |
|  | 1600 | 0 | −100 | −200 | −200 | −300 | −300 | 0 | 300 |
| HR | 105 | 0 | 0 | 0 | −5 | −10 | −15 | −10 | −5 |
|  | 125 | −5 | −5 | −5 | −5 | −10 | −15 | −15 | −10 |
|  | 125 | 0 | 0 | 0 | 0 | −5 | −15 | −10 | 0 |
|  | 115 | 0 | 0 | 0 | 0 | −5 | 5 | 10 | 15 |

2. Averages: (n = 4)

|  | | TIME (min) | | | | | | |
|---|---|---|---|---|---|---|---|---|
|  | bv | 5 | 10 | 15 | 30 | 60 | 120 | 180 | 240 |
| BPs | 135 | −5 | −18 | −26 | −30 | −33 | −31 | −24 | −12 |
| average SEM | 6 | 2 | 1 | 3 | 4 | 7 | 6 | 5 | 4 |
| BPd | 86 | −4 | −11 | −16 | −20 | −20 | −20 | −15 | −7 |
| average SEM | 4 | 1 | 1 | 1 | 2 | 4 | 4 | 4 | 5 |
| LVEDP | 11 | −0 | −2 | −2 | −2 | −3 | −4 | −4 | −4 |
| average SEM | 1 | 0 | 1 | 1 | 1 | 0 | 1 | 1 | 1 |
| dp/dt | 1300 | 0 | −100 | −125 | −150 | −200 | −250 | −150 | 25 |
| average SEM | 108 | 0 | 0 | 25 | 29 | 71 | 29 | 65 | 95 |
| HR | 118 | −1 | −1 | −1 | −2 | −8 | −10 | −6 | 0 |
| average SEM | 5 | 1 | 1 | 1 | 1 | 1 | 5 | 6 | 5 |

TABLE X.B

Second administration of compound (46)

1. Parameters:

|  | bv | 5 | 10 | 15 | 30 | 60 | 120 |
|---|---|---|---|---|---|---|---|
| BPs | 115 | −5 | −15 | −20 | −25 | −30 | −20 |
|  | 125 | −10 | −15 | −20 | −20 | −30 | −30 |
|  | 120 | −5 | −5 | −15 | −20 | −20 | −20 |
|  | 140 | −5 | −10 | −15 | −35 | −50 | −35 |
| BPd | 70 | −5 | −10 | −15 | −15 | −15 | −10 |
|  | 75 | −5 | −5 | −10 | −10 | −15 | −15 |
|  | 80 | −5 | −5 | −5 | −10 | −10 | −10 |
|  | 95 | −5 | −5 | −10 | −25 | −35 | −25 |
| LVEDP | 5 | 0 | 0 | −1 | −1 | −1 | −1 |
|  | 7 | 0 | 0 | −1 | −1 | −1 | −1 |
|  | 3 | 1 | 0 | 2 | 0 | −1 | −2 |
|  | 10 | 0 | 0 | 0 | −2 | −3 | −3 |
| dp/dt | 1000 | 0 | 0 | −100 | −100 | −100 | −100 |
|  | 1200 | 0 | 0 | −100 | −100 | −200 | −200 |
|  | 1200 | −100 | −100 | 0 | −100 | −200 | −200 |
|  | 2200 | −100 | −200 | −300 | −600 | −900 | −600 |
| HR | 100 | 0 | 0 | −5 | 0 | −5 | 0 |
|  | 115 | 0 | 0 | 0 | −5 | −10 | −15 |
|  | 125 | 0 | 0 | 0 | 0 | 0 | 0 |
|  | 130 | 0 | 0 | 0 | 0 | 0 | 5 |

2. Averages: (n = 4)

|  | | TIME (min) | | | | | |
|---|---|---|---|---|---|---|---|
|  | bv | 5 | 10 | 15 | 30 | 60 | 120 |
| BPs | 125 | −6 | −11 | −18 | −25 | −33 | −26 |
| average SEM | 5 | 1 | 2 | 1 | 4 | 6 | 4 |
| BPd | 80 | −5 | −6 | −10 | −15 | −19 | −15 |
| average SEM | 5 | 0 | 1 | 2 | 4 | 6 | 4 |
| LVEDP | 6 | 0 | 0 | 0 | −1 | −2 | −2 |
| average SEM | 1 | 0 | 0 | 1 | 0 | 1 | 0 |
| dp/dt | 1400 | −50 | −75 | −125 | −225 | 350 | −275 |
| average SEM | 271 | 29 | 48 | 63 | 125 | 185 | 111 |
| HR | 118 | 0 | 0 | −1 | −1 | −4 | −2 |
| average SEM | 7 | 0 | 0 | 1 | 1 | 2 | 4 |

On the first administration, IS05-MN in a dosage of 5 mg/kg and compound (46) in a dosage of 0.75 mg/kg induce, on average, a similar fall (−30 mmHg) in the BPs.

The maximum effect is obtained 5 minutes after the administration in the case of IS-5-MN and 60 minutes after in the case of compound (46). The period of action of compound (46) is longer, for which reason the interval between the first and the second administration is 4 hours. The second administration of IS-5-MN gives rise to a fall in the BP which reaches its maximum after 5 min (−19 mmHg) followed by a rapid return to the control value. The second administration of compound (46) gives rise to a fall in the BP which reaches its maximum after 60 min (−33 mmHg).

The study is discontinued 120 minutes after the second administration.

These results confirm the previous data with regard to IS-5-MN (development of tachyphylaxis after repeated administration), in dogs.

They also show the absence of the development of tachyphylaxis after the administration of (46).

As can be seen from the above, the invention is in no way restricted to those of its implementations, embodiments and applications which have Just been described more explicitly; on the contrary, it encompasses all of the variants which may be envisaged by a person skilled in the art, without going beyond either the framework or the scope of the present invention.

We claim:

1. Organic nitrates, of to the following formula I:

R—CO—A—YB    (I)

in which:

R represents

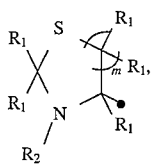  (radical C)

in which radical C:
R$_1$ represents a hydrogen atom, a (straight-chain, branched or cyclic) C$_1$ to C$_6$ alkyl group, an optionally substituted phenyl or an optionally substituted benzyl;

R$_2$ represents a hydrogen atom, a (straight-chain, branched or cyclic) C$_1$ to C$_6$ alkyl group, an optionally substituted phenyl, an optionally substituted benzyl, a C$_1$-C$_6$ acyl group, an optionally substituted benzoyl, an alkoxycarbonyl or a CO—X group in which X represents a radical C and m represents 1 or 2;

A represents a CH$_2$ group, an amino acid, group with the acid group bonded to Y and the amino group bonded to CO, or one of the following radicals:

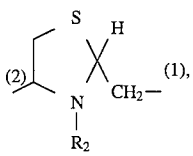  (radical H)

in which radical H:
R$_2$ represents a hydrogen atom, a (straight-chain, branched or cyclic) C$_1$ to C$_6$ alkyl group, an optionally substituted phenyl, an optionally substituted benzyl, a C$_1$ to C$_6$ acyl group, an optionally substituted benzoyl, an alkoxycarbonyl group or a group CO—X in which X represents one of the radicals C, D, E, F or G as defined above for R, (1) is the bond with Y, and
(2) is the bond with R—CO; or

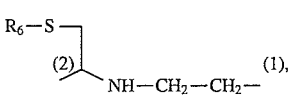  (radical I)

in which radical I:
R$_6$ represents a hydrogen atom, a (straight-chain, branched or cyclic) C$_1$ to C$_6$ alkyl group, an optionally substituted phenyl, a substituted S-phenyl, an optionally substituted benzyl or one of the following groups: CH$_3$—CO—NH—CH$_2$, S—CH$_2$—CH—(CO—R$_7$)—NH—CH$_2$—CH$_2$—NH—B in which R$_7$ represents an OH group, a C$_1$-C$_6$ O-alkyl group, an optionally substituted O-phenyl group, an optionally substituted O-benzyl group, a radical E as defined above or a radical Y—B, B and Y being as defined below, and (1) and (2) have the same meaning as above;

Y represents an oxygen atom or an NH group;

B represents:
α) a 1,4:3,6-dianhydro hexitol mononitrate radical of formula (a)

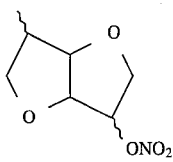

β) a C$_1$ to C$_6$ itol nitrate radical of formulae (b) and

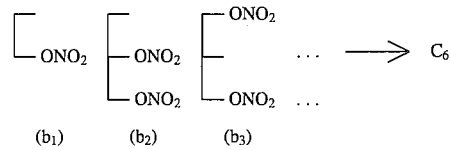

γ) an inositol "p"-nitrate radical, p being an integer from 1 to 5, of formula (c)

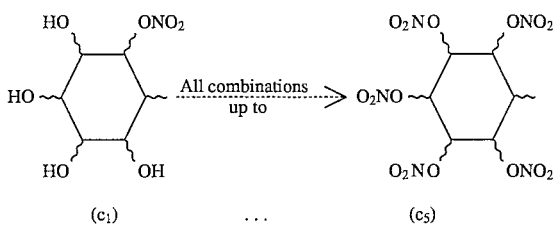

δ) one of the following groups:
a —CH$_2$—C(CH$_2$—ONO$_2$)$_3$ group, derived from pentaerythritol,
a —CH$_2$—C(C$_2$H$_5$)(CH$_2$—ONO$_2$)$_2$ group, derived from ethyltrimethylolmethane, or
a —CH$_2$—CH$_2$—N(CH$_2$—CH$_2$—ONO$_2$)$_2$ group, derived from triethanolamine,
with all OH and ONO$_2$ combinations.

2. Organic nitrates according to claim 1, characterised in that they contain the following radicals for R, A, Y and B respectively:

R represents one of the following radicals:

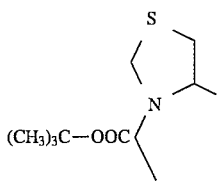

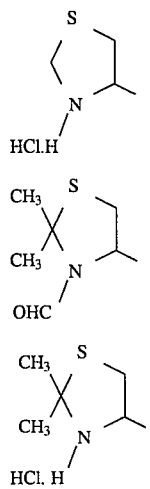

A represents an optionally substituted amino acid radical;

Y represents an oxygen atom or an NH group; and

B is a radical derived from the following compounds:

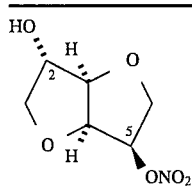 1,4:3,6-dianhydro-D-glucitol 5-nitrate

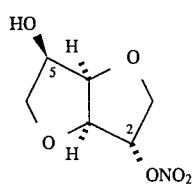 1,4:3,6-dianhydro-D-glucitol 2-nitrate

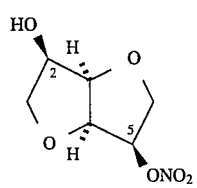 1,4:3,6-dianhydro-D-mannitol 5-nitrate

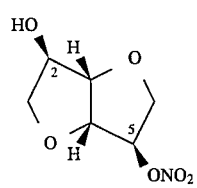 1,4:3,6-dianhydro-D-iditol 5-nitrate

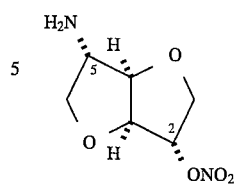 5-amino-1,4:3,6-dianhydro-5-deoxy-L-iditol 2-nitrate

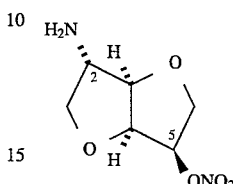 2-amino-1,4:3,6-dianhydro-2-deoxy-D-glucitol 5-nitrate

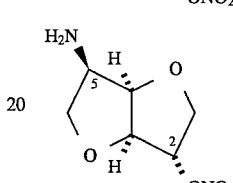 5-amino-1,4:3,6-dianhydro-5-deoxy-D-glucitol 2-nitrate

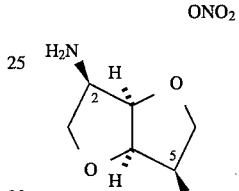 2-amino-1,4:3,6-dianhydro-2-deoxy-D-mannitol 5-nitrate.

3. Organic nitrate according to claim 1, characterised in that it corresponds to 5-[[2-[[(3-formyl-2,2-dimethyl-4-L-thiazolidinyl)carbonyl]amino]-1-oxoethyl]amino]-5-deoxy-2-O-nitro-1,4:3,6-dianhydro-L-iditol (48).

4. Medicament, characterised in that it comprises at least one organic nitrate according to claim 1, alone or in combination with one or more pharmaceutically compatible active principles and/or adjuvants.

5. 5-[[2-[[(3-t-butoxycarbonyl-4-L-thiazolidinyl)carbonyl]amino]-1-((2S)-2-methyl)-oxoethyl]amino]-5-deoxy-2-O-nitro-1,4:3,6-dianhydro-L-iditol (61).

6. Organic nitrate according to claim 1 characterised in that it corresponds to 5-[[2-[[(4-L-thiazolidinyl)carbonyl]amino]-1-oxoethyl]amino]-5-deoxy-2-O-nitro-1,4:3,6-dianhydro-L-iditol monohydrochloride (46).

7. Organic nitrates according to claim 2 in which the amino acid radical A is selected from the group consisting of glycine and its derivatives, proline and its derivatives, alanine and its derivatives, valine and its derivatives and phenylalanine and its derivatives.

* * * * *